United States Patent
Gallant et al.

(10) Patent No.: US 6,627,656 B2
(45) Date of Patent: Sep. 30, 2003

(54) METHOD OF TREATMENT USING PHENYL AND BIARYL DERIVATIVES AS PROSTAGLANDIN E INHIBITORS AND COMPOUNDS USEFUL THEREFORE

(76) Inventors: Michel Gallant, Merck & Co., Inc., P.O. Box 2000, Rahway, NJ (US) 07065-0907; Nicolas Lachance, Merck & Co., Inc., P.O. Box 2000, Rahway, NJ (US) 07065-0907; Marc Labelle, Merck & Co., Inc., P.O. Box 2000, Rahway, NJ (US) 07065-0907; Robert Zamboni, Merck & Co., Inc., P.O. Box 2000, Rahway, NJ (US) 07065-0907; Helene Juteau, Merck & Co., Inc., P.O. Box 2000, Rahway, NJ (US) 07065-0907; Yves Gareau, Merck & Co., Inc., P.O. Box 2000, Rahway, NJ (US) 07065-0907; Patrick Lacombe, Merck & Co., Inc., P.O. Box 2000, Rahway, NJ (US) 07065-0907

( * ) Notice: Subject to any disclaimer, the term of this patent is extended or adjusted under 35 U.S.C. 154(b) by 0 days.

(21) Appl. No.: 09/840,942

(22) Filed: Apr. 24, 2001

(65) Prior Publication Data

US 2002/0082266 A1 Jun. 27, 2002

Related U.S. Application Data

(60) Provisional application No. 60/199,299, filed on Apr. 24, 2000.

(51) Int. Cl.$^7$ ............... A61K 31/21; A61P 29/00; C07C 69/76; C07D 419/00; C07D 235/08
(52) U.S. Cl. ............... 514/506; 514/517; 514/532; 514/539; 560/8; 560/11; 560/21; 560/55; 560/59; 560/102; 544/333; 544/335; 546/152; 546/192; 548/304.4; 549/229; 549/240
(58) Field of Search ............... 514/506, 517, 514/532, 539; 560/8, 11, 21, 55, 59, 102; 544/333, 335; 546/152, 192; 548/304.4; 549/229, 240

(56) References Cited

U.S. PATENT DOCUMENTS 6,242,493 B1 * 6/2001 Gareau et al. ............... 514/569

FOREIGN PATENT DOCUMENTS

| WO | WO 94/02474 | 2/1994 |
|----|-------------|--------|
| WO | WO 95/03295 | 2/1995 |
| WO | WO 96/30358 | 10/1996 |
| WO | WO 99/47497 | 9/1999 |
| WO | WO 00/20371 | 4/2000 |

* cited by examiner

Primary Examiner—Mukund J. Shah
Assistant Examiner—Tamthom N. Truong
(74) Attorney, Agent, or Firm—Raynard Yuro; David L. Rose

(57) ABSTRACT

This invention encompasses a method for the treatment or prevention of prostaglandin mediated diseases comprising administering to a mammalian patient a compound of formula I:

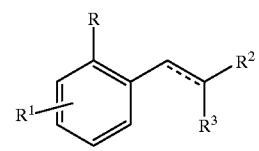

in an amount that is effective to treat or prevent said prostaglandin mediated disease. Novel compounds are also disclosed.

5 Claims, No Drawings

METHOD OF TREATMENT USING PHENYL AND BIARYL DERIVATIVES AS PROSTAGLANDIN E INHIBITORS AND COMPOUNDS USEFUL THEREFORE

CROSS-REFERENCE TO RELATED APPLICATIONS

This application claims the benefit of U.S. Provisional Application No. 60/199,299, filed on Apr. 24, 2000.

BACKGROUND OF THE INVENTION

This invention relates to methods for treating prostaglandin mediated diseases. More particularly, the compounds are antagonists of the pain and inflammatory effects of E-type prostaglandins. Additionally preferred compounds are included.

Two review articles describe the characterization and therapeutic relevance of the prostanoid receptors as well as the most commonly used selective agonists and antagonists: *Eicosanoids: From Biotechnology to Therapeutic Applications*, Folco, Samuelsson, Maclouf, and Velo eds, Plenum Press, New York, 1996, chap. 14, 137–154 and Journal of Lipid Mediators and Cell Signalling, 1996, 14, 83–87. An article from *The British Journal of Pharmacology* (1994, 112, 735–740) suggests that Prostaglandin $E_2$ ($PGE_2$) exerts allodynia through the $EP_1$ receptor subtype and hyperalgesia through $EP_2$ and $EP_3$ receptors in the mouse spinal cord.

Thus, selective prostaglandin ligands, agonists or antagonists, depending on which prostaglandin E receptor subtype is being considered, have anti-inflammatory, antipyretic and analgesic properties similar to a conventional non-steroidal anti-inflammatory drug, and in addition, inhibit hormone-induced uterine contractions and have anticancer effects. These compounds have a diminished ability to induce some of the mechanism-based side effects of NSAIDs which are indiscriminate cyclooxygenase inhibitors. In particular, the compounds have a reduced potential for gastrointestinal toxicity, a reduced potential for renal side effects, a reduced effect on bleeding times and a lessened ability to induce asthma attacks in aspirin-sensitive asthmatic subjects.

In The American Physiological Society (1994, 267, R289-R-294), studies suggest that PGE2-induced hyperthermia in the rat is mediated predominantly through the EP1 receptor. World patent applications WO 96/06822 (Mar. 7, 1996), WO 96/11902 (Apr. 25, 1996) and EP 752421-A1 (Jan. 8, 1997) disclose compounds as being useful in the treatment of prostaglandin mediated diseases.

SUMMARY OF THE INVENTION

A method of treating or preventing a prostaglandin E mediated disease is described which comprises administering to a mammalian patient in need of such treatment or prevention a compound of formula I:

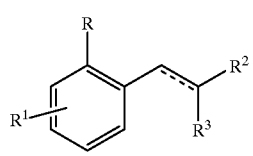

wherein:
R is a group Ar as defined hereinafter;
$R^1$ is hydrogen, hydroxy, $C_{1-6}$alkyl, $C_{1-6}$alkoxy, $X(CH_2)_pAr$, or a methylenedioxy group attached to two adjacent ring carbon atoms;
$R^2$ is —$(CH_2)_xC(O)N(R^4)S(O)_yR^5$, —$(CH_2)_xS(O)_yN(R^4)C(O)R^5$, —$(CH_2)_xC(O)N(R^4)C(O)R^5$, —$(CH_2)_xS(O)_yN(R^4)S(O)_yR^5$, —$(CH_2)_xCO_2R^4$, or tetrazol-5-yl optionally substituted by $C_{1-6}$alkyl;
$R^3$ is $X(CH_2)_pAr$ or $X(CH_2)_pR^4$ or a group of formula (a):

(a)

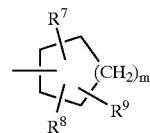

Ar is a group of formula (b) or (c):

(b)

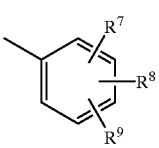

(c)

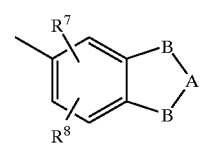

or Ar is naphthyl, indolyl, pyridyl, thienyl, furyl, oxazolidinyl, oxazolyl, thiazolyl, isothiazolyl, pyrazolyl, thriazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidinyl, all of which may be unsubstituted or substituted by one or more $R^7$ or $R^8$ groups;
A is C=O or $(C(R^4)_2)_m$;
each B is independently —$CH_2$— or —O—;
$R^4$ is hydrogen or $C_{1-6}$alkyl;
$R^5$ is hydrogen or $C_{1-10}$alkyl or Ar, both of which may be unsubstituted or substituted by one or two Cl, F, Br, hydroxy, $XC_{1-5}$alkyl, $C_{1-5}$alkyl, $NO_2$, tetrazol-5-yl optionally substituted by $C_{1-6}$alkyl, or $R^5$ is $N(R^4)_2$;
$R^6$ is hydrogen, $R^{10}$, $CO_2R^{11}$, $CO_2C(R^{10})_2O(CO)XR^{11}$, $PO_3(R^{11})_2$, $SO_2NR^{11}R^{10}$, $NR^{11}SO_2R^{10}$, $CONR^{11}SO_2R^{10}$, $SO_3R^{11}$, $S(O)_qR^{11}$, $S(O)_qN(R^{11})C(O)R^{10}$, $S(O)_qN(R^{11})S(O)_qR^{10}$, $C(O)N(R^{11})C(O)R^{10}$, $N(R^{11})C(O)R^{10}$, $N(R^{11})_p$, $N(R^{11})C(O)NR^{11}$, $P(O)(OR^{11})R^{11}$, CN, —$CO_2(CH_2)_mC(O)N(R^4)_2$, $C(R^{10})_2N(R^{11})_2$, $C(O)N(R^4)_2$, $OR^4$ or tetrazolyl optionally substituted by C1–6 alkyl;
$R^7$ and $R^9$ are independently hydrogen, $R^{10}$, OH, $C_{1-8}$alkoxy, $S(O)_qR^{10}$, $N(R^4)_2$, Br, F, I, Cl, $CF_3$, $NO_2$, $NHCOR^4$, $R^{12}CO_2R^{11}$, —X—$R^{13}$—Y, —$X(CR^4)_pOR^4$, $S(CH_2)_pCO_2H$, $(CH_2)_pX$—$R^{13}$, —$X(CH_2)_pCONR^{11}SO_2R^{10}$, $(CH_2)_pXCONR^{11}SO_2R^{10}$ or $X(CH_2)_p$ $R^6$ wherein each methylene group within —$X(CH_2)_q$ $R^6$ may be unsubstituted or substituted by one or two —$(CH_2)_pAr$ groups;
$R^8$ is hydrogen, $R^{10}$, OH, $C_{1-5}$alkoxy, $S(O)_qR^{10}$, $N(R^4)_2$, Br, F, I, Cl or $NHCOR^4$ wherein the $C_{1-5}$ alkoxy may be unsubstituted or substituted by OH, methoxy or halogen;

$R^{10}$ is hydrogen, Ar, $C_{1-10}$alkyl, $C_{2-10}$alkenyl, $C_{2-10}$alkynyl, all of which may be unsubstituted or substituted by one or more OH, .$CH_2OH$, $N(R^4)_2$ or halogen; or $R^{10}$ is $N(R^4)_2$;

$R^{11}$ is independently hydrogen, $C_{1-10}$alkyl, $C_{2-10}$alkenyl or $C_{2-8}$alkynyl, all of which may be unsubstituted or substituted by one or more OH, $N(R^4)_2$, $CO_2R^{14}$, halogen or $XC_{1-5}$alkyl; or $R^{11}$ is $(CH_2)_pAr$;

$R^{12}$ is divalent Ar, $C_{1-10}$alkylene, $C_{1-10}$alkylidene, $C_{2-10}$alkenylene, $C_{2-10}$alkynylene, all of which may be unsubstituted or substituted by one or more of OH, $CH_2OH$, $N(R^4)_2$ or halogen;

$R^{13}$ is a bond, $C_{1-10}$alkylene, $C_{1-10}$alkenylene, $C_{1-10}$alkylidene, $C_{1-10}$alkynylene, all of which may be linear or branched, or phenylene, all of which may be unsubstituted or substituted by one or more OH, $N(R^4)_2$, COOH or halogen;

$R^{14}$ is hydrogen, $C_{1-6}$alkyl, $C_{2-6}$alkenyl or $C_{2-7}$alkynyl;

X is $(CH_2)_p$, O, $NR^4$ or $S(O)_p$;

Y is $CH_3$ or $X(CH_2)_pAr$;

q is zero, one or two;

p is an integer from 0 to 6;

m is 1, 2 or 3;

n is 1 to 4;

x is 0 to 4;

y is 1 or 2;

the dotted line signifies the optional presence of a bond such that it represents a single or double bond.

DETAILED DESCRIPTION

In one aspect of the invention, a method of treating or preventing a prostaglandin E mediated disease is described which comprises administering to a mammalian patient in need of such treatment or prevention a compound of formula I:

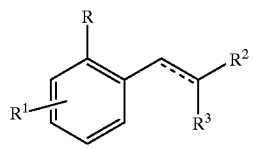

I wherein:

R is a group Ar as defined hereinafter;

$R^1$ is hydrogen, hydroxy, $C_{1-6}$alkyl, $C_{1-6}$alkoxy, $X(CH_2)_p$Ar, or a methylenedioxy group attached to two adjacent ring carbon atoms;

$R^2$ is —$(CH_2)_xC(O)N(R^4)S(O)_yR^5$, —$(CH_2)_xS(O)_yN(R^4)C(O)R^5$, —$(CH_2)_xC(O)N(R^4)C(O)R^5$, —$(CH_2)_xS(O)_yN(R^4)S(O)_yR^5$, —$(CH_2)_xCO_2R^4$, or tetrazol-5-yl optionally substituted by $C_{1-6}$alkyl;

$R^3$ is $X(CH_2)_pAr$ or $X(CH_2)_pR^4$ or a group of formula (a):

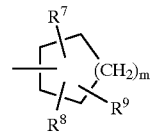

(a)

Ar is a group of formula (b) or (c):

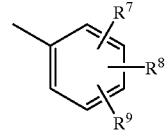

(b)

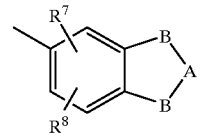

(c)

or Ar is naphthyl, indolyl, pyridyl, thienyl, furyl, oxazolidinyl, oxazolyl, thiazolyl, isothiazolyl, pyrazolyl, thriazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidinyl, all of which may be unsubstituted or substituted by one or more $R^7$ or $R^8$ groups;

A is C=O or $(C(R^4)_2)_m$;

each B is independently —$CH_2$— or —O—;

$R^4$ is hydrogen or $C_{1-6}$alkyl;

$R^5$ is hydrogen or $C_{1-10}$alkyl or Ar, both of which may be unsubstituted or substituted by one or two Cl, F, Br, hydroxy, $XC_{1-5}$alkyl, $C_{1-5}$alkyl, $NO_2$, tetrazol-5-yl optionally substituted by $C_{1-6}$alkyl, or $R^5$ is $N(R^4)_2$;

$R^6$ is hydrogen, $R^{10}$, $CO_2R^{11}$, $CO_2C(R^{10})_2O(CO)XR^{11}$, $PO_3(R^{11})_2$, $SO_2NR^{11}R^{10}$, $NR^{11}SO_2R^{10}$, $CONR^{11}SO_2R^{10}$, $SO_3R^{11}$, $S(O)_qR^{11}$, $S(O)_qN(R^{11})C(O)R^{10}$, $S(O)_qN(R^{11})S(O)_qR^{10}$, $C(O)N(R^{11})C(O)R^{10}$, $N(R^{11})C(O)R^{10}$, $N(R^{11})_2$, $N(R^{11})C(O)NR^{11}$, $P(O)(OR^{11})R^{11}$, CN, —$CO_2(CH_2)_mC(O)N(R^4)_2$, $C(R^{10})_2N(R^{11})_2$, $C(O)N(R^4)_2$, $OR^4$ or tetrazolyl optionally substituted by C1–6 alkyl;

$R^7$ and $R^9$ are independently hydrogen, $R^{10}$, OH, $C_{1-8}$alkoxy, $S(O)_qR^{10}$, $N(R^4)_2$, Br, F, I, Cl, $CF_3$, $NO_2$, $NHCOR^4$, $R^{12}CO_2R^{11}$, —X—$R^{13}$—Y, —$X(CR^4)_p$ $OR^4$, $S(CH_2)_pCO_2H$, $(CH_2)_pX$—$R^{13}$, —$X(CH_2)_p$ $CONR^{11}SO_2R^{10}$, $(CH_2)_pXCONR^{11}SO_2R^{10}$ or $X(CH_2)_p$ $R^6$ wherein each methylene group within —$X(CH_2)_q$ $R^6$ may be unsubstituted or substituted by one or two —$(CH_2)_p$Ar groups;

$R^8$ is hydrogen, $R^{10}$, OH, $C_{1-5}$alkoxy, $S(O)_qR^{10}$, $N(R^4)_2$, Br, F, I, Cl or $NHCOR^4$ wherein the $C_{1-5}$ alkoxy may be unsubstituted or substituted by OH, methoxy or halogen;

$R^{10}$ is hydrogen, Ar, $C_{1-10}$alkyl, $C_{2-10}$alkenyl, $C_{2-10}$alkynyl, all of which may be unsubstituted or substituted by one or more OH, .$CH_2OH$, $N(R^4)_2$ or halogen; or $R^{10}$ is $N(R^4)_2$;

$R^{11}$ is independently hydrogen, $C_{1-10}$alkyl, $C_{2-1}$alkenyl or $C_{2-8}$alkynyl, all of which may be unsubstituted or substituted by one or more OH, $N(R^4)_2$, $CO_2R^{14}$, halogen or $XC_{1-5}$alkyl; or $R^{11}$ is $(CH_2)_pAr$;

$R^{12}$ is divalent Ar, $C_{1-10}$alkylene, $C_{1-10}$alkylidene, $C_{2-10}$alkenylene, $C_{2-10}$alkynylene, all of which may be unsubstituted or substituted by one or more of OH, $CH_2OH$, $N(R^4)_2$ or halogen;

$R^{13}$ is a bond, $C_{1-10}$alkylene, $C_{1-10}$alkenylene, $C_{1-10}$alkylidene, $C_{1-10}$alkynylene, all of which may be linear or branched, or phenylene, all of which may be unsubstituted or substituted by one or more OH, $N(R^4)_2$, COOH or halogen;

$R^{14}$ is hydrogen, $C_{1-6}$ alkyl, $C_{2-6}$ alkenyl or $C_{2-7}$ alkynyl;

X is $(CH_2)_p$, O, $NR^4$ or $S(O)_p$;

Y is $CH_3$ or $X(CH_2)_pAr$;

q is zero, one or two;

p is an integer from 0 to 6;

m is 1, 2 or 3;

n is 1 to 4;

x is 0 to 4;

y is 1 or 2;

the dotted line signifies the optional presence of a bond such that it represents a single or double bond.

An embodiment of the invention that is of particular interest relates to a method of treating or preventing a prostaglandin mediated disease comprising administering to a mammalian patient in need of such treatment a compound of formula I in an amount which is effective for treating or preventing a prostaglandin mediated disease, wherein the prostaglandin mediated disease is selected from the group consisting of:

(1) pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures as well as immune and autoimmune diseases;

(2) cellular neoplastic transformations or metastic tumor growth;

(3) diabetic retinopathy and tumor angiogenesis;

(4) prostanoid-induced smooth muscle contraction associated with dysmenorrhea, premature labor, asthma or eosinophil related disorders;

(5) Alzheimer's disease;

(6) glaucoma;

(7) bone loss;

(8) osteoporosis;

(9) promotion of bone formation;

(10) Paget's disease;

(11) cytoprotection in peptic ulcers, gastritis, regional enteritis, ulcerative colitis, diverticulitis or other gastrointestinal lesions;

(12) GI bleeding and patients undergoing chemotherapy;

(13) coagulation disorders selected from hypoprothrombinemia, haemophilia and other bleeding problems;

(14) kidney disease;

(15) thrombosis;

(16) occlusive vascular disease;

(17) presurgery; and

(18) anti-coagulation.

Another embodiment of the invention is a method of treating or preventing prostaglandin mediated disease comprising administering to a mammalian patient in need of such treatment a compound of formula I in an amount which is effective for treating or preventing a prostaglandin mediated disease, wherein the prostaglandin mediated disease is selected from the group consisting of: pain, fever or inflammation associated with rheumatic fever, influenza or other viral infections, common cold, low back and neck pain, skeletal pain, postpartum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures as well as immune and autoimmune diseases.

Another embodiment of the invention is a method of treating or preventing a prostaglandin mediated disease comprising administering to a mammalian patient in need of such treatment a compound of formula I in an amount which is effective for treating or preventing a prostaglandin mediated disease, wherein the prostaglandin mediated disease is pain, fever or inflammation associated with dysmenorrhea.

Another embodiment of the invention is a method of treating or preventing a prostaglandin mediated disease comprising administering to a mammalian patient in need of such treatment a compound of formula I in an amount which is effective for treating or preventing a prostaglandin mediated disease, wherein the compound is co-administered with other agents or ingredients.

Another embodiment of the invention is a method of treating or preventing a prostaglandin mediated disease comprising administering to a mammalian patient in need of such treatment a compound of formula I in an amount which is effective for treating or preventing a prostaglandin mediated disease, wherein the compound is co-administered with another agent or ingredient selected from the group consisting of:

(1) an analgesic selected from acetaminophen, phenacetin, aspirin, a narcotic;

(2) a cyclooxygenase-2 selective nonsteroidal antiinflammatory drug or a conventional nonsteroidal antiinflammatory drug;

(3) caffeine;

(4) an $H_2$-antagonist;

(5) aluminum or magnesium hydroxide;

(6) simethicone;

(7) a decongestant selected from phenylephrine, phenylpropanolamine, pseudophedrine, oxymetazoline, ephinephrine, naphazoline, xylometazoline, propylhexedrine, or levo-desoxyephedrine;

(8) an antiitussive selected from codeine, hydrocodone, caramiphen, carbetapentane and dextramethorphan;

(9) another prostaglandin ligand selected from misoprostol, enprostil, rioprostil, omoprostol and rosaprostol; a diuretic; and

(10) a sedating or non-sedating antihistamine. Examples of COX-2 inhibitors are disclosed in U.S. Pat. Nos. 5,474,995; 5,633,272; and 5,466,823; and in WO 96/25405, WO 97/38986, WO 98/03484, WO 97/14691, and WO 95/0051.

Another embodiment of the invention is a method of treating or preventing a prostaglandin mediated disease comprising administering to a mammalian patient in need of such treatment a compound of formula I in an amount which is effective for treating or preventing a prostaglandin mediated disease, wherein the compound is co-administered with a cyclooxygenase-2 selective nonsteroidal anti-inflammatory drug or a conventional nonsteroidal anti-inflammatory drug.

Another embodiment of the invention is a method of treating or preventing a prostaglandin mediated disease comprising administering to a mammalian patient in need of such treatment a compound of formula I in an amount which is effective for treating or preventing a prostaglandin mediated disease, wherein the compound is co-administered with a conventional nonsteroidal anti-inflammatory drug selected from the group consisting of: aspirin, ibuprofen, naproxen, and ketoprofen.

Another embodiment of the invention is a method of treating or preventing a prostaglandin mediated disease comprising administering to a mammalian patient in need of such treatment a compound of formula I in an amount which is effective for treating or preventing a prostaglandin mediated disease, wherein the compound is co-administered with a cyclooxygenase-2 selective nonsteroidal anti-inflammatory drug selected from rofecoxib and celecoxib.

Preferred subsets of compounds and species that are useful for the methods described herein are set forth in WO96/30358, incorporated by reference.

Additional preferred species for use in treating prostaglandin mediated diseases or conditions include the following:

TABLE 1

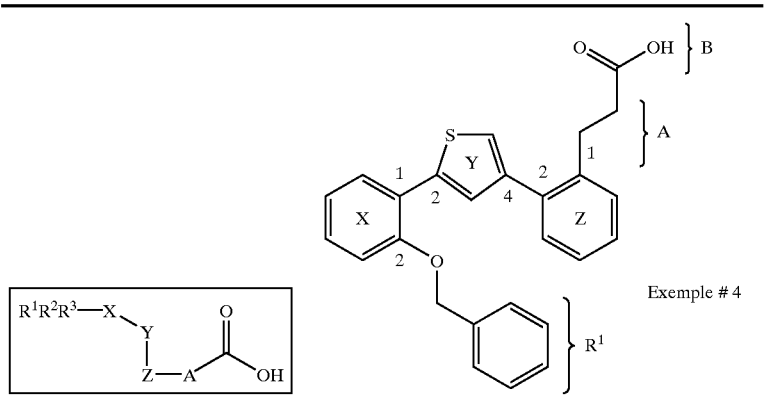

| $R^1$ | $R^2$ | $R^3$ | X | $Y(R^{7,8})$ | $Z(R^{7,8})$ | A | Cpd |
|---|---|---|---|---|---|---|---|
| 2-(2,6-Cl$_2$-benzyloxy) | H | H | benzene diyl | 1,3 benzene diyl | 1,2 benzene diyl | CH$_2$—CH$_2$ | 1 |
| 2-Benzyloxy | H | H | benzene diyl | 1,3 benzene diyl | 1,2 benzene diyl | CH$_2$—CH(CH$_3$) | 2 |
| 2-Benzyloxy | H | H | benzene diyl | 2,5-thiophene diyl | 1,2 benzene diyl | CH$_2$—CH$_2$ | 3 |
| 2-Benzyloxy | H | H | benzene diyl | 4,2-thiophene diyl | 1,2 benzene diyl | CH$_2$—CH$_2$ | 4 |
| 2-Benzyloxy | 5-Cl | H | 3-pyridine triyl | 1,3 benzene diyl | 1,2 benzene diyl | CH$_2$—CH$_2$ | 5 |
| 2-Benzyloxy | H | H | benzene diyl | 2,4-thiophene triyl (5-Cl) | 1,2 benzene diyl | CH$_2$—CH$_2$ | 6 |
| 2-Benzyloxy | H | H | benzene diyl | 1,3 benzene diyl | 1,2 benzene diyl | CH=CH | 7 |
| 2-Benzyloxy | H | H | benzene diyl | 3,5-pyridine diyl | 1,2 benzene diyl | CH=CH | 8 |
| 2-(2,6-Cl$_2$-benzyloxy) | H | H | benzene diyl | 2,4-thiophene diyl | 1,2 benzene diyl | CH$_2$—CH$_2$ | 9 |
| 2-Benzyloxy | H | H | benzene diyl | 4,2-thiophene diyl | 1,2 benzene diyl | CH$_2$—CH(CH$_3$) | 10 |
| H | H | H | naphthyl | 1,3 benzene diyl | 1,2 benzene diyl | CH$_2$—CH$_2$ | 11 |
| H | H | H | phenyl | 1,3 benzene diyl | 1,2 benzene diyl | CH$_2$—CH$_2$ | 12 |
| 2-Benzyloxy | H | H | benzene diyl | 1,3 benzene diyl | 1,2 benzene diyl | CH$_2$—CH$_2$—CH$_2$ | 13 |
| 2-Chloro | 3-Cl | H | benzene triyl | 1,3 benzene diyl | 1,2 benzene diyl | CH$_2$—CH$_2$ | 14 |
| 2-Benzyloxy | H | H | benzene diyl | 2,4-thiophene diyl | 1,2 benzene diyl | CH$_2$—CH$_2$ | 15 |
| 2-Phenoxymethyl | H | H | benzene diyl | 1,3 benzene diyl | 1,2 benzene diyl | CH$_2$—CH$_2$ | 16 |
| 4-Benzyloxy | H | H | benzene diyl | 1,3 benzene diyl | 1,2 benzene diyl | CH$_2$—CH$_2$ | 17 |
| 4-Benzyloxy | H | H | 1-naphthalenediyl | 1,3 benzene diyl | 1,2 benzene diyl | CH$_2$—CH$_2$ | 18 |
| 2-Benzyl | H | H | benzene | 2,5-thiophene | 1,2 benzene | CH=CH | 19 |

TABLE 1-continued

| R¹ | R² | R³ | X | Y(R⁷,⁸) | Z(R⁷,⁸) | A | Cpd |
|---|---|---|---|---|---|---|---|
| 2-Benzyloxy | H | H | benzene diyl | 2,4-thiophene diyl | 1,2 benzene diyl | CH=CH | 20 |
| 2-Benzyloxy | H | H | benzene diyl | 1,3 benzene diyl | 1,2 benzene diyl | CH₂—CH₂ | 21 |
| 2-Benzyloxy | 4-F | 5-F | benzene tetrayl | 3,5-thiophene diyl | 1,2 benzene diyl | CH₂—CH₂ | 22 |
| 2-Benzyloxy | 3-F | 5-F | benzene tetrayl | 3,5-thiophene diyl | 1,2 benzene diyl | CH=CH | 23 |
| 4-Benzyloxy | H | H | benzene diyl | 3,5-thiophene diyl | 1,2 benzene diyl | CH=C(CH₃) | 24 |
| 4-Benzyloxy | 3-OMe | H | benzene triyl | 1,4-imidazole diyl | 1,2 benzene diyl | CH₂—CH₂ | 25 |
| 2-Benzyloxy | H | H | benzene diyl | 2,4-thiazole diyl | 1,2 benzene diyl | CH=CH | 26 |
| 2-(4-MeO-benzyloxy) | H | H | benzene diyl | 2,5-thiazole diyl | 1,2 benzene diyl | CH=C(CH₃) | 27 |
| 2-(4-CF₃-benzyloxy) | H | H | benzene diyl | 4,2-thiazole diyl | 1,2 benzene diyl | CH₂—CH₂ | 28 |
| 2-(4-F-benzyloxy) | H | H | benzene diyl | 5,2-thiazole diyl | 1,2 benzene diyl | CH=CH | 29 |
| 2-Benzyloxy | H | H | benzene diyl | 2,4-oxazole diyl | 1,2 beuzene diyl | CH=C(CH₃) | 30 |
| 2-(4-MeO-benzyloxy) | H | H | benzene diyl | 2,5-oxazole diyl | 1,2 benzene diyl | CH₂—CH₂ | 31 |
| 2-(4-CF₃-benzyloxy) | H | H | benzene diyl | 4,2-oxazole diyl | 1,2 benzene diyl | CH=CH | 32 |
| 2-(4-F-benzyloxy) | H | H | benzene diyl | 5,2-oxazole diyl | 1,2 benzene diyl | CH=C(CH₃) | 33 |
| 2-Benzyloxy | H | H | benzene diyl | 2,4-pyrimidine diyl | 1,2 benzene diyl | CH₂—CH₂ | 34 |
| 2-(4-MeO-benzyloxy) | H | H | benzene diyl | 4,6-pyrimidine diyl | 1,2 benzene diyl | CH=CH | 35 |
| 2-(4-CF₃-benzyloxy) | H | H | benzene diyl | 4,2-pyrimidine diyl | 1,2 benzene diyl | CH=C(CH₃) | 36 |
| 2-(4-F-benzyloxy) | H | H | benzene diyl | 6,4-pyrimidine diyl | 1,2 benzene diyl | CH₂—CH₂ | 37 |
| 2-Benzyloxy | H | H | benzene diyl | 2,6-pyridine diyl | 1,2 benzene diyl | CH=CH | 38 |
| N-benzyl | H | H | 3-indole diyl | 1,3-benzene diyl | 1,2 benzene triyl (3-Cl) | CH=C(CH₃) | 39 |
| N-benzyl | H | H | 7-indole diyl | 1,3-benzene diyl | 1,2 benzene triyl (3-OMe) | CH₂—CH₂ | 40 |
| 2-Benzyloxy | H | H | benzene diyl | 1,3-benzene triyl (5-Cl) | 1,2 benzene triyl (4-F) | CH=CH | 41 |
| 2-Benzyloxy | H | H | benzene diyl | 1,3-benzene triyl (5-OCF₃) | 1,2 benzene triyl (4-Cl) | CH=C(CH₃) | 42 |
| 2-Benzyloxy | H | H | benzene diyl | 1,3-benzene triyl (5-CN) | 1,2 benzene triyl (5-Cl) | CH₂—CH₂ | 43 |
| 2-Benzyloxy | H | H | benzene diyl | 1,3-benzene triyl (5-Me) | 1,2 benzene triyl (5-OMe) | CH=CH | 44 |
| 2-Benzyloxy | H | H | benzene diyl | 1,3-benzene triyl (2-Me) | 1,2 benzene triyl (6-Cl) | CH=C(CH₃) | 45 |
| 2-Benzyloxy | H | H | benzene diyl | 1,3-benzene triyl (2-OMe) | 1,2 benzene triyl (6-OMe) | CH₂—CH₂ | 46 |
| 3-Benzyloxy | H | H | 2-pyridine diyl | 1,3-benzene diyl | 1,2 benzene diyl | CH=CH | 47 |

TABLE 1-continued

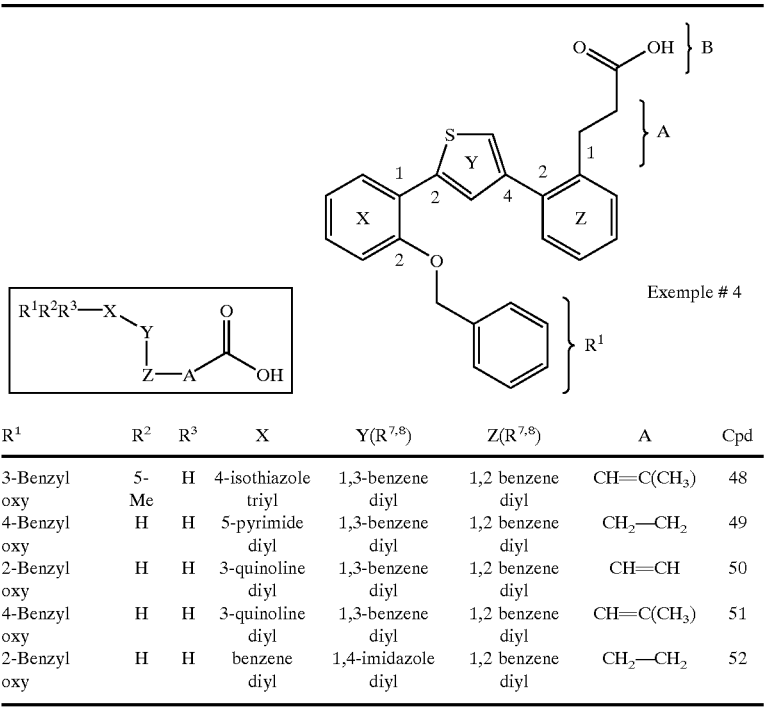

Exemple # 4

| R[1] | R[2] | R[3] | X | Y(R[7,8]) | Z(R[7,8]) | A | Cpd |
|---|---|---|---|---|---|---|---|
| 3-Benzyloxy | 5-Me | H | 4-isothiazole triyl | 1,3-benzene diyl | 1,2 benzene diyl | CH=C(CH$_3$) | 48 |
| 4-Benzyloxy | H | H | 5-pyrimide diyl | 1,3-benzene diyl | 1,2 benzene diyl | CH$_2$—CH$_2$ | 49 |
| 2-Benzyloxy | H | H | 3-quinoline diyl | 1,3-benzene diyl | 1,2 benzene diyl | CH=CH | 50 |
| 4-Benzyloxy | H | H | 3-quinoline diyl | 1,3-benzene diyl | 1,2 benzene diyl | CH=C(CH$_3$) | 51 |
| 2-Benzyloxy | H | H | benzene diyl | 1,4-imidazole diyl | 1,2 benzene diyl | CH$_2$—CH$_2$ | 52 |

TABLE 2

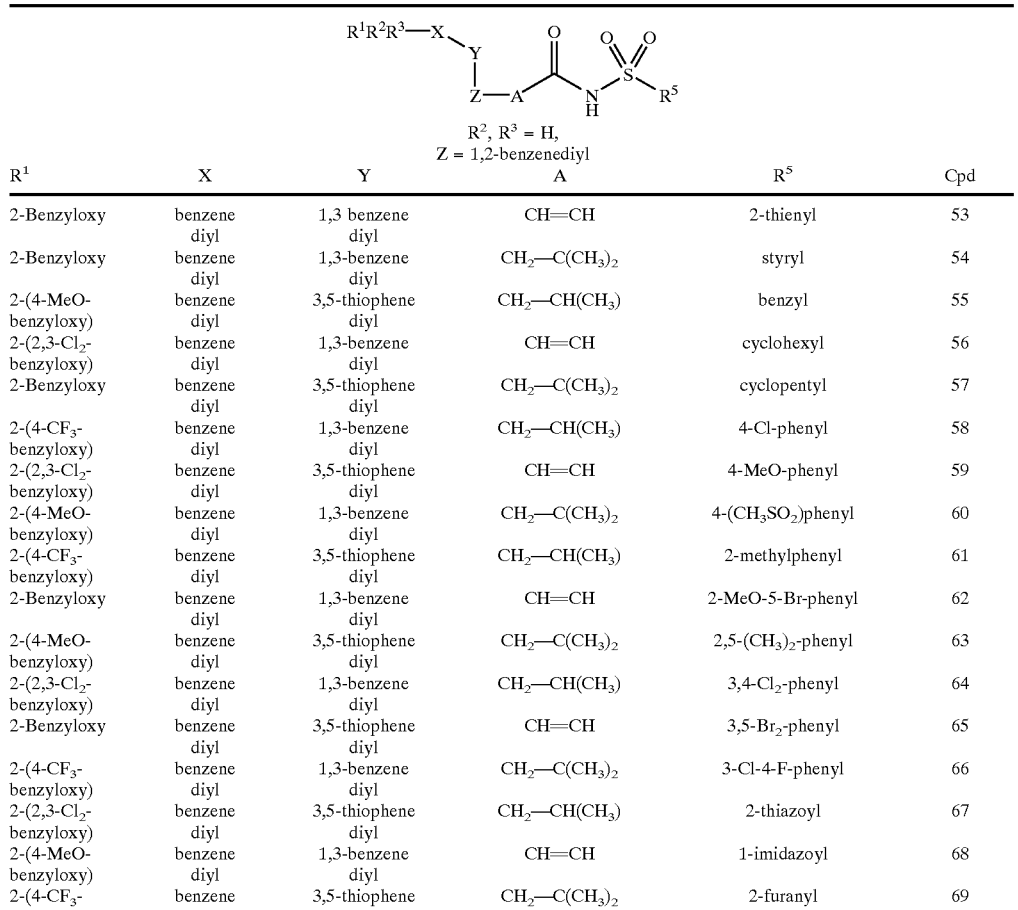

$R^2$, $R^3$ = H,
Z = 1,2-benzenediyl

| R[1] | X | Y | A | R[5] | Cpd |
|---|---|---|---|---|---|
| 2-Benzyloxy | benzene diyl | 1,3 benzene diyl | CH=CH | 2-thienyl | 53 |
| 2-Benzyloxy | benzene diyl | 1,3-benzene diyl | CH$_2$—C(CH$_3$)$_2$ | styryl | 54 |
| 2-(4-MeO-benzyloxy) | benzene diyl | 3,5-thiophene diyl | CH$_2$—CH(CH$_3$) | benzyl | 55 |
| 2-(2,3-Cl$_2$-benzyloxy) | benzene diyl | 1,3-benzene diyl | CH=CH | cyclohexyl | 56 |
| 2-Benzyloxy | benzene diyl | 3,5-thiophene diyl | CH$_2$—C(CH$_3$)$_2$ | cyclopentyl | 57 |
| 2-(4-CF$_3$-benzyloxy) | benzene diyl | 1,3-benzene diyl | CH$_2$—CH(CH$_3$) | 4-Cl-phenyl | 58 |
| 2-(2,3-Cl$_2$-benzyloxy) | benzene diyl | 3,5-thiophene diyl | CH=CH | 4-MeO-phenyl | 59 |
| 2-(4-MeO-benzyloxy) | benzene diyl | 1,3-benzene diyl | CH$_2$—C(CH$_3$)$_2$ | 4-(CH$_3$SO$_2$)phenyl | 60 |
| 2-(4-CF$_3$-benzyloxy) | benzene diyl | 3,5-thiophene diyl | CH$_2$—CH(CH$_3$) | 2-methylphenyl | 61 |
| 2-Benzyloxy | benzene diyl | 1,3-benzene diyl | CH=CH | 2-MeO-5-Br-phenyl | 62 |
| 2-(4-MeO-benzyloxy) | benzene diyl | 3,5-thiophene diyl | CH$_2$—C(CH$_3$)$_2$ | 2,5-(CH$_3$)$_2$-phenyl | 63 |
| 2-(2,3-Cl$_2$-benzyloxy) | benzene diyl | 1,3-benzene diyl | CH$_2$—CH(CH$_3$) | 3,4-Cl$_2$-phenyl | 64 |
| 2-Benzyloxy | benzene diyl | 3,5-thiophene diyl | CH=CH | 3,5-Br$_2$-phenyl | 65 |
| 2-(4-CF$_3$-benzyloxy) | benzene diyl | 1,3-benzene diyl | CH$_2$—C(CH$_3$)$_2$ | 3-Cl-4-F-phenyl | 66 |
| 2-(2,3-Cl$_2$-benzyloxy) | benzene diyl | 3,5-thiophene diyl | CH$_2$—CH(CH$_3$) | 2-thiazoyl | 67 |
| 2-(4-MeO-benzyloxy) | benzene diyl | 1,3-benzene diyl | CH=CH | 1-imidazoyl | 68 |
| 2-(4-CF$_3$- | benzene | 3,5-thiophene | CH$_2$—C(CH$_3$)$_2$ | 2-furanyl | 69 |

TABLE 2-continued
$$R^1R^2R^3-X\underset{Z-A}{\overset{Y}{\diagdown}}\underset{H}{\overset{O}{\diagdown}}\underset{\overset{\|}{O}}{\overset{\|}{\overset{\|}{S}}}R^5$$
$R^2, R^3 = H,$
$Z = 1,2\text{-benzenediyl}$
| $R^1$ | X | Y | A | $R^5$ | Cpd |
|---|---|---|---|---|---|
| benzyloxy) | diyl | diyl | | | |
| 2-Benzyloxy | benzene diyl | 1,3-benzene diyl | $CH_2—CH(CH_3)$ | 3-indolyl | 70 |
| 2-(4-CF$_3$- benzyloxy) | benzene diyl | 3,5-thiophene diyl | CH=CH | 2-quinolinyl | 71 |
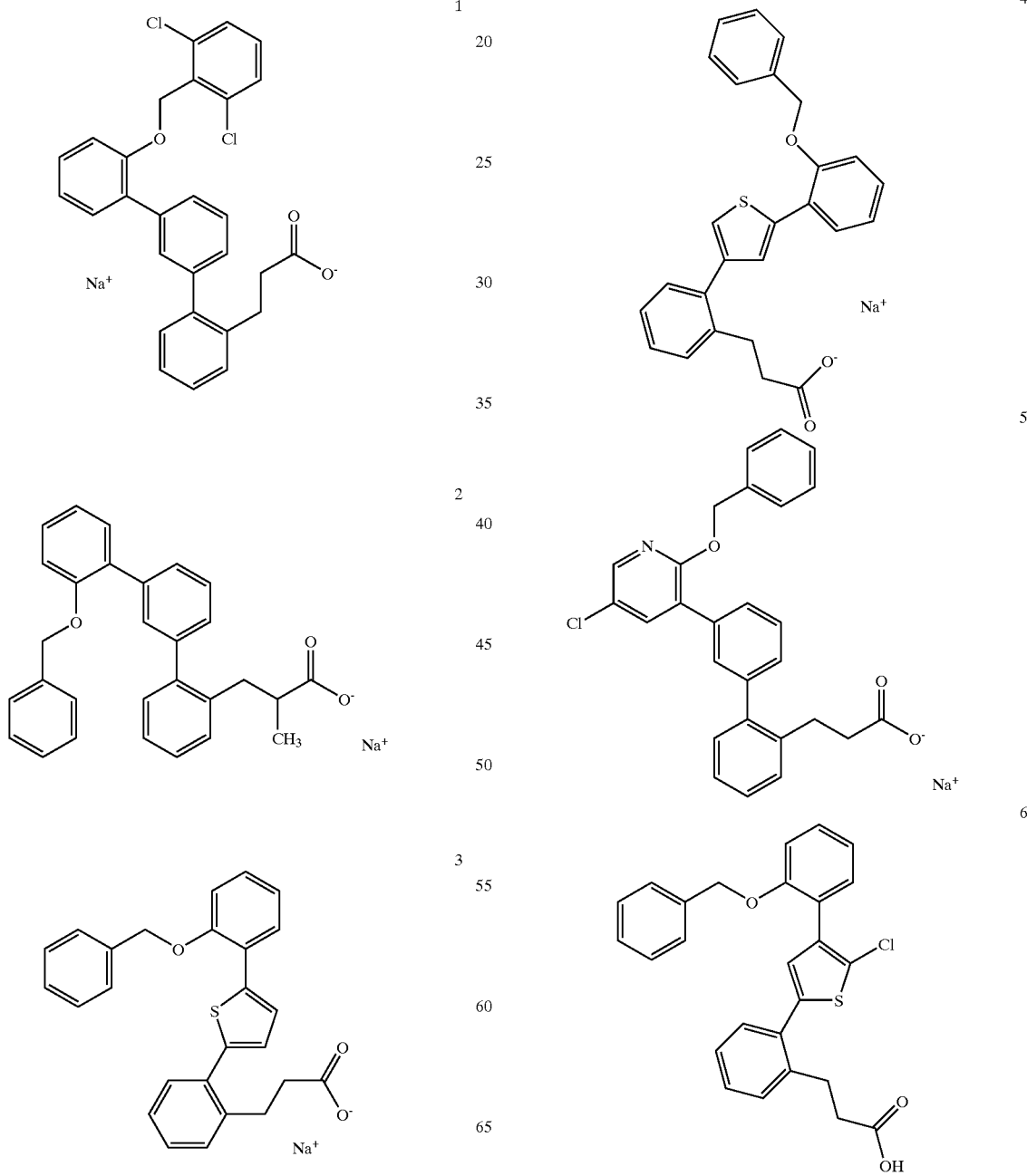

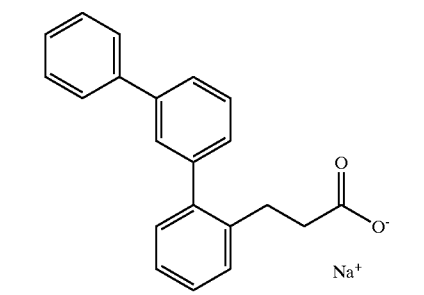
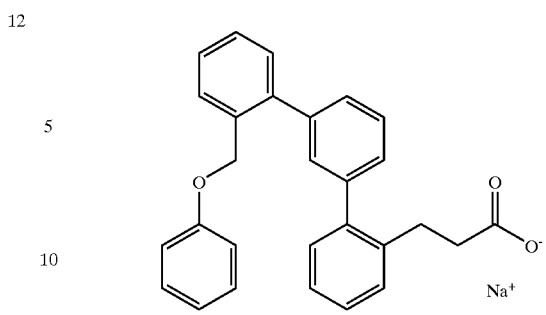
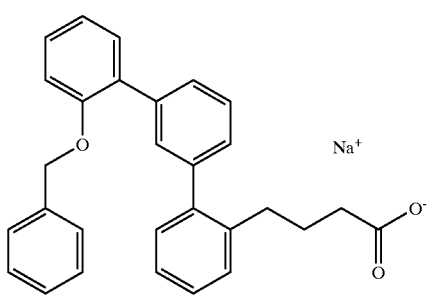
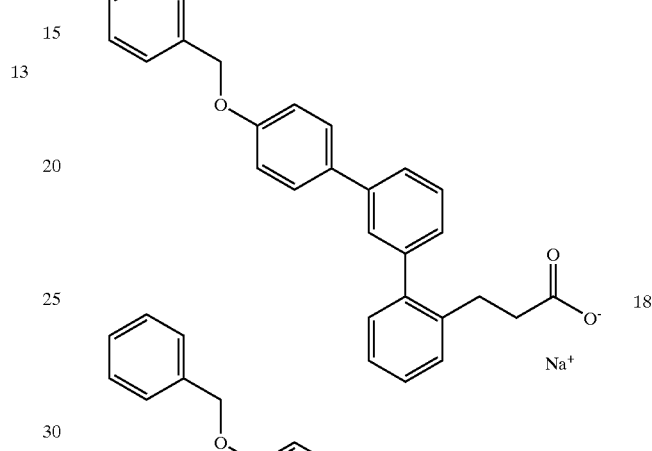
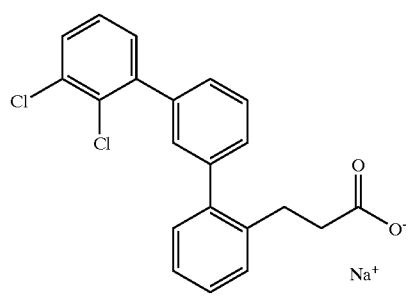
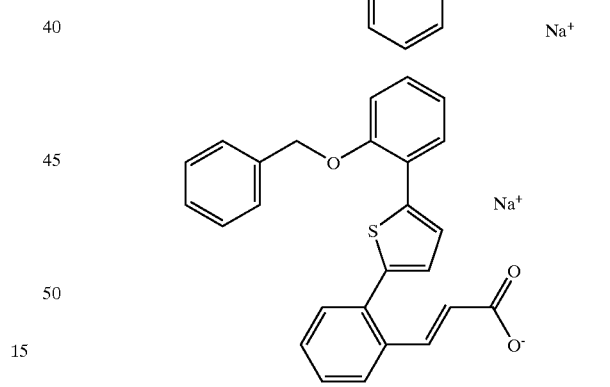
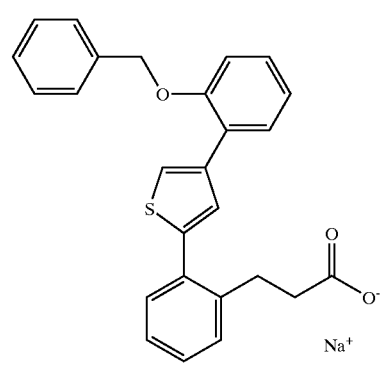
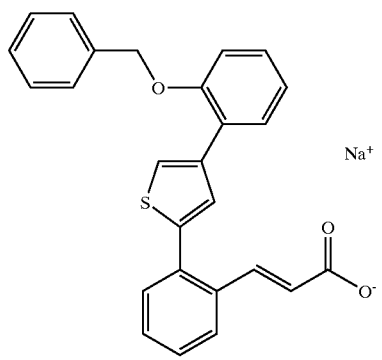

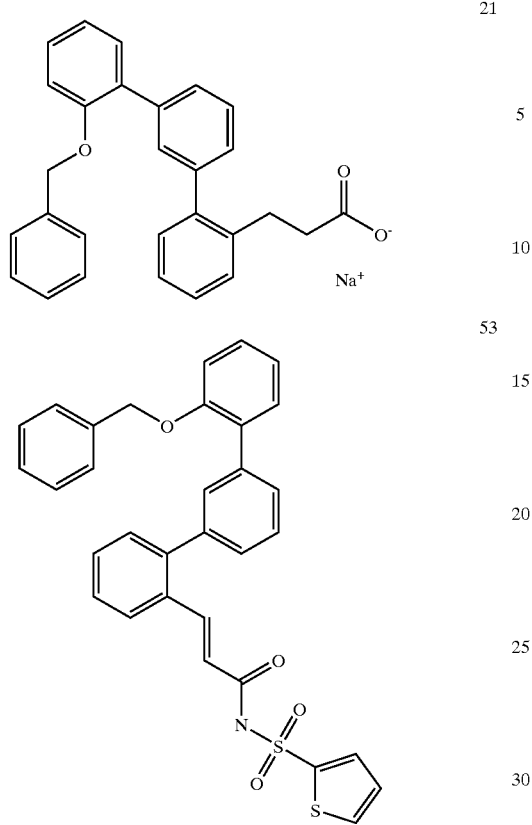

Representative compounds having a sulfonamide group are shown below.

TABLE 3

| R¹ | R² | X | Y($R^{7,8}$) | A | B | Cpd |
|---|---|---|---|---|---|---|
| 3-(2-Ph—Et—SCH$_2$) | H | benzene diyl | 1,2 benzene diyl | CH$_2$—CH$_2$ | 2-thienyl | 72 |
| 4-(2-Ph—Et—SCH$_2$) | H | benzene diyl | 1,2 benzene diyl | CH$_2$—CH$_2$ | 2-thienyl | 73 |
| 4-(2-Ph—Et—SCH$_2$) | H | benzene diyl | 1,2 benzene diyl | CH$_2$—CH$_2$—CH$_2$ | 2-thienyl | 74 |
| 4-(3(-3-(2-Ph—Et—SCH$_2$)Ph-oxy)Pr-oxy) | H | benzene diyl | 1,2 benzene diyl | CH$_2$—CH$_2$ | 2-thienyl | 75 |
| 4-(3(-3-(2-Ph—Et—S(O)—CH$_2$)Ph-oxy)Pr-oxy) | H | benzene diyl | 1,2 benzene diyl | CH$_2$—CH$_2$ | 2-thienyl | 76 |
| 4-(3-(3-Me—Ph-oxy)Pr-oxy) | H | benzene diyl | 1,2 benzene diyl | CH$_2$—CH$_2$ | 2-thienyl | 77 |
| 4-(3(-3-(2-Ph—Et—S(O)$_2$—CH$_2$)Ph-oxy)Pr-oxy) | H | benzene diyl | 1,2 benzene diyl | CH$_2$—CH$_2$ | 2-thienyl | 78 |
| 4-Carbazole-yl-CH$_2$ | H | benzene diyl | 1,2 benzene diyl | CH$_2$—CH$_2$ | 2-thienyl | 79 |
| 4-(2-Ph—Et—SCH$_2$) | H | benzene diyl | 1,2 benzene triyl (5-Bn) | CH$_2$—CH$_2$ | 2-thienyl | 80 |

TABLE 3-continued

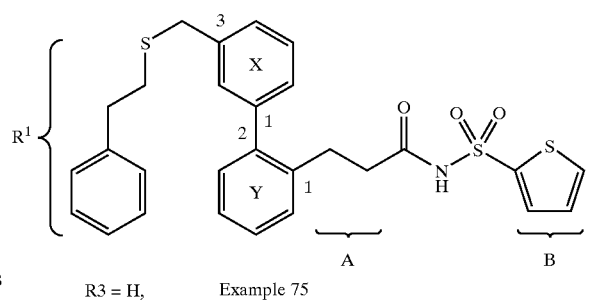

R3 = H, Example 75

| R¹ | R² | X | Y(R⁷,⁸) | A | B | Cpd |
|---|---|---|---|---|---|---|
| 4-(3-(3-Me—Ph-oxy)Pr-oxy) | H | benzene diyl | 1,2 benzene diyl | CH₂—CH(CH₃) | 2-thienyl | 81 |
| 4-(3-(3-Ph)Pr-oxy CH₂)Ph-oxy)Pr-oxy) | H | benzene diyl | 1,2 benzene diyl | CH₂—CH₂ | 2-thienyl | 82 |
| 4-(3-(2-(Qn)ethenyl)Ph-oxy)Pr-oxy) | H | benzene diyl | 1,2 benzene diyl | CH₂—CH₂ | 2-thienyl | 83 |
| 4-(3-(3-2-((4-Cl-Ph)—Et)Ph-oxy)Pr-oxy) | H | benzene diyl | 1,2 benzene diyl | CH₂—CH₂ | 2-thienyl | 84 |
| 4-(3-(3-(4-Ph—Ph-oxy-CH₂)Ph-oxy)Pr-oxy) | H | benzene diyl | 1,2 benzene diyl | CH₂—CH₂ | 2-thienyl | 85 |
| 3-(3-(3-Me—Ph-oxy)Pr-oxy) | H | benzene diyl | 1,2 benzene diyl | CH₂—CH₂ | 2-thienyl | 86 |
| 4-(2-(3-Tolyl)acetoxy CH₂) | H | benzene diyl | 1,2 benzene diyl | CH₂—CH₂ | 2-thienyl | 87 |
| 4-(2-(3-Tolyl)acetamide CH₂) | H | benzene diyl | 1,2 benzene diyl | CH₂—CH₂ | 2-thienyl | 88 |
| 3-(3-(2-(Qn) CH₂ oxy) | H | benzene diyl | 1,2 benzene diyl | CH₂—CH₂ | 2-thienyl | 89 |
| 3-Thiomethyl | H | benzene diyl | 1,2 benzene diyl | CH₂—CH₂ | 2-thienyl | 90 |
| 3-Methylsulfone | H | benzene diyl | 1,2 benzene diyl | CH₂—CH₂ | 2-thienyl | 91 |
| 4-(3-(3-Me—Ph-oxy)Pr-oxy) | 3,5-Br | benzene tetrayl | 1,2 benzene diyl | CH₂—CH₂ | 2-thienyl | 92 |
| 3-(3-(2-(Qn)ethenyl)Ph-oxy)Pr-oxy) | H | benzene diyl | 1,2 benzene diyl | CH₂—CH₂ | 2-thienyl | 93 |
| 3-(2-(Qn)ethenyl) | H | benzene diyl | 1,2 benzene diyl | CH₂—CH₂ | 2-thienyl | 94 |
| 3-(3-(3-Me—Ph-oxy)Pr-oxy) | H | benzene diyl | 1,2 benzene diyl | CH₂—CH((CH₂)₃Ph) | 2-thienyl | 95 |
| 3-(2-Ph-2-oxy-ethoxy) | H | benzene diyl | 1,2 benzene diyl | CH₂—CH₂ | 2-thienyl | 96 |
| 3-(2-(3-Phenyl-Pr-oxy)2-Ph-ethoxy) | H | benzene diyl | 1,2 benzene diyl | CH₂—CH₂ | 2-thienyl | 97 |
| 3-(2-(Qn)ethenyl) | H | benzene diyl | 1,2 benzene diyl | CH=CH | 2-thienyl | 98 |
| 4-Chloro | 3-Cl | benzene triyl | 1,2 benzene diyl | CH=CH | 2-thienyl | 99 |
| 3-(2-(Qn)ethenyl) | H | benzene diyl | 1,2 benzene triyl (5-CF₃) | CH=CH | 2-thienyl | 100 |
| 3-(3-(3-Me—Ph-oxy)Pr-oxy) | H | benzene diyl | 1,2 benzene triyl (5-OMe) | CH=CH | 2-MeO-5-Br-phenyl | 101 |
| 4-Chloro | 3-Cl | benzene triyl | 1,2 benzene triyl (5-Me) | CH=CH | 3-Cl-4-F-phenyl | 102 |
| 3-(2-Ph—Et—SCH₂) | H | benzene diyl | 1,2 benzene triyl (5-Bn) | CH=CH | 2-thienyl | 103 |
| 3-(2-(Qn)ethenyl) | H | benzene diyl | 1,2 benzene triyl (6-Cl) | CH=CH | 2-MeO-5-Br—Ph | 104 |
| 3-(3-(3-Me—Ph-oxy)Pr-oxy) | H | benzene diyl | 1,2 benzene triyl (6-OMe) | CH=CH | 3-Cl-4-F-phenyl | 105 |
| 4-Chloro | 3-Cl | benzene triyl | 1,2 benzene triyl (3-Cl) | CH=CH | 2-thienyl | 106 |
| 3-(2-Ph—Et—SCH₂) | H | benzene diyl | 1,2 benzene triyl (3-OMe) | CH=CH | 2-MeO-5-Br—Ph | 107 |
| 3-(2-(Qn)ethenyl) | H | benzene diyl | 1,2 benzene triyl (4-F) | CH=CH | 3-Cl-4-F-phenyl | 108 |

TABLE 3-continued

| R¹ | R² | X | Y(R⁷,⁸) | A | B | Cpd |
|---|---|---|---|---|---|---|
| 3-(3-(3-Me—Ph-oxy)Pr-oxy) | H | benzene diyl | 1,2 benzene triyl (4-Cl) | CH=CH | 2-thienyl | 109 |
| 4-Chloro | 3-Cl | benzene triyl | 1,2 benzene diyl | CH=CH | 4-MeO-phenyl | 110 |
| 3-Ph—Et—SCH₂ | H | benzene diyl | 1,2 benzene diyl | CH=CH | 4-CF₃-phenyl | 111 |
| 3-(2-(Qn)ethenyl) | H | benzene diyl | 1,2 benzene diyl | CH=CH | 4-(CH₃SO₂) phenyl | 112 |
| 3-(3-(3-Me—Ph-oxy)Pr-oxy) | H | benzene diyl | 1,2 benzene diyl | CH=CH | 2-methyl phenyl | 113 |
| 4-Chloro | 3-Cl | benzene triyl | 1,2 benzene diyl | CH=CH | 2,3-Cl₂-phenyl | 114 |
| 3-(2-Ph-Et—SCH₂) | H | benzene diyl | 1,2 benzene diyl | CH=CH | 2-NO₂-4-Cl-phenyl | 115 |
| 3-(2-(Qn)ethenyl) | H | benzene diyl | 1,2 benzene diyl | CH=CH | 2,5-(CH₃)₂-phenyl | 116 |
| 3-(3-(3-Me—Ph-oxy)Pr-oxy) | H | benzene diyl | 1,2 benzene diyl | CH=CH | 2,6-F₂-phenyl | 117 |
| 4-Chloro | H | benzene diyl | 1,2 benzene diyl | CH=CH | 3,4-Cl₂-phenyl | 118 |
| 3-(2-Ph-Et—SCH₂) | H | benzene diyl | 1,2 benzene diyl | CH=CH | 3,5-Br₂-phenyl | 119 |
| 3-(2-(Qn)ethenyl) | H | benzene diyl | 1,2 benzene diyl | CH=CH | 2-thiazoyl | 120 |
| 4-Bn | H | 2-thiophene diyl | 1,2 benzene diyl | CH=CH | 4-oxazoyl | 121 |
| 2-(4-MeO-benzyl) | H | 4-thiophene diyl | 1,2 benzene diyl | CH=CH | 1-imidazoyl | 122 |
| 4-(2,3-Cl₂-benzyl) | H | 1-imidazole diyl | 1,2 benzene diyl | CH=CH | 2-furanyl | 123 |
| 1-(4-CF₃-benzyl) | H | 4-imidazole diyl | 1,2 benzene diyl | CH=CH | 2-pyridinyl | 124 |
| 4-(4-F-benzyl) | H | 2-thiazole diyl | 1,2 benzene diyl | CH=CH | 3-indolyl | 125 |
| 5-Bn | H | 2-thiazole diyl | 1,2 benzene diyl | CH=CH | 2-quinolinyl | 126 |
| 2-(4-MeO-benzyl) | H | 4-thiazole diyl | 1,2 benzene diyl | CH=CH | 2-thienyl | 127 |
| 2-(2,3-Cl₂-benzyl) | H | 5-thiazole diyl | 1,2 benzene diyl | CH=CH | 2-thienyl | 128 |
| 4-(4-CF₃-benzyl) | H | 2-oxazole diyl | 1,2 benzene diyl | CH=CH | 2-thienyl | 129 |
| 5-(4-F-benzyl) | H | 2-oxazole diyl | 1,2 benzene diyl | CH=CH | 2-thienyl | 130 |
| 2-(2-Ph-Et—SCH₂) | H | 4-oxazole diyl | 1,2 benzene diyl | CH=CH | 2-thienyl | 131 |
| 2-Bn | H | 5-oxazole diyl | 1,2 benzene diyl | CH=CH | 2-thienyl | 132 |
| 4-(4-MeO-benzyl) | H | 2-pyrimidine diyl | 1,2 benzene diyl | CH=CH | 2-thienyl | 133 |
| 5-(2,3-Cl₂-benzyl) | H | 2-pyrimidine diyl | 1,2 benzene diyl | CH=CH | 2-thienyl | 134 |
| 6-(4-CF₃-benzyl) | H | 2-pyrimidine diyl | 1,2 benzene diyl | CH=CH | 2-thienyl | 135 |
| 2-(4-F-benzyl) | H | 4-pyrimidine diyl | 1,2 benzene diyl | CH=CH | 2-thienyl | 136 |
| 2-(2-Ph-Et—SCH₂) | H | 6-pyridine diyl | 1,2 benzene diyl | CH=CH | 2-thienyl | 137 |
| 6-Bn | H | 4-pyrimidine diyl | 1,2 benzene diyl | CH=CH | 2-thienyl | 138 |
| 4-(4-MeO-benzyl) | H | 6-pyrimidine | 1,2 benzene | CH=CH | 2-thienyl | 139 |

TABLE 3-continued
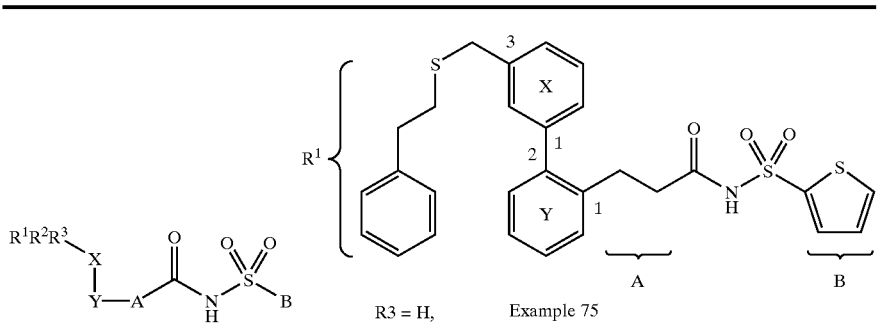
| R¹ | R² | X | Y(R⁷,⁸) | A | B | Cpd |
|---|---|---|---|---|---|---|
| N—Bn | H | 3-indole diyl | 1,2 benzene diyl | CH=CH | 2-thienyl | 140 |
| N—Bn | H | 7-indole diyl | 1,2 benzene diyl | CH=CH | 2-thienyl | 141 |
| 2-Benzyloxy | H | 6-pyridine diyl | 1,2 benzene diyl | CH=CH | 2-thienyl | 142 |
Qn = 7-chloro-quinol-2-yl
2-Ph—Et—SMe = 2-phenylethylthiomethyl
3-(3-Me—Ph-oxy)Pr-oxy = 3-(3-methylphenoxy)propyl-1-oxy
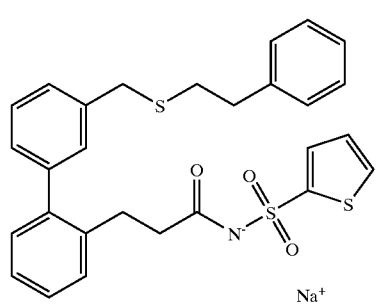
72
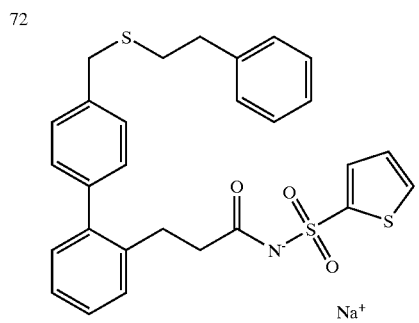
73
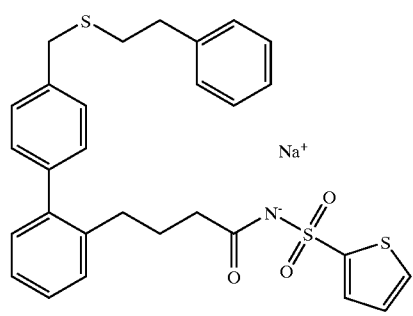
74
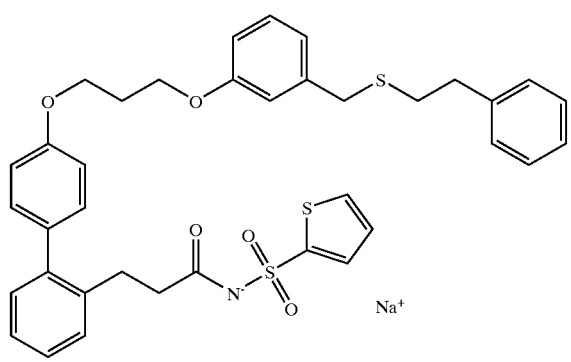
75

-continued
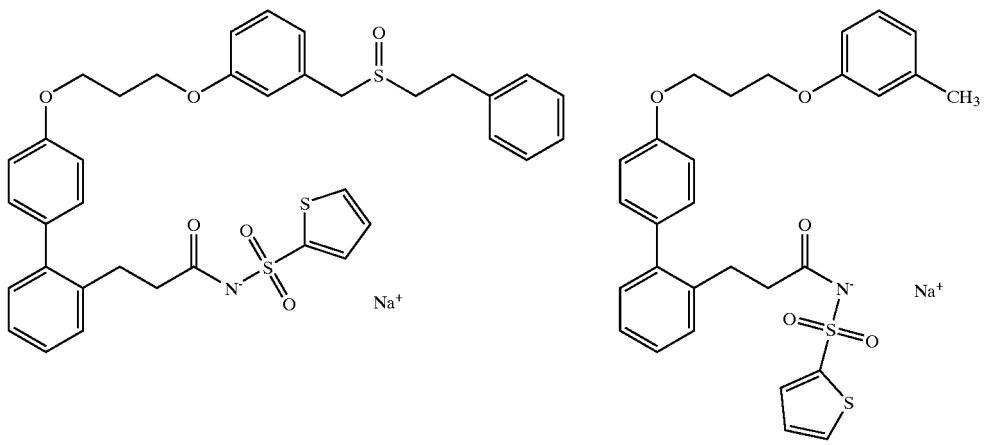
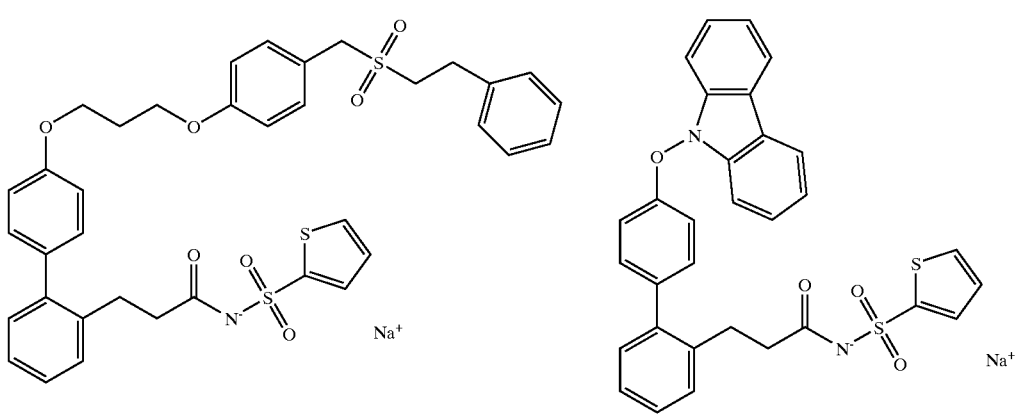
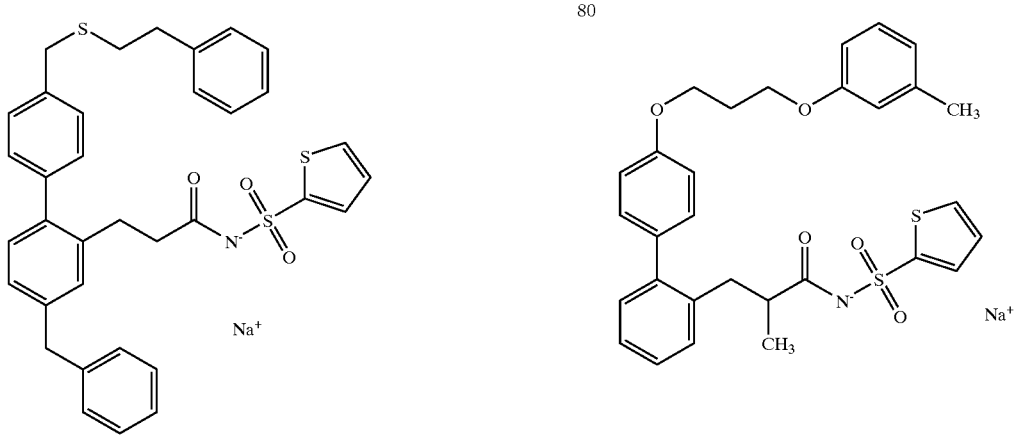

-continued
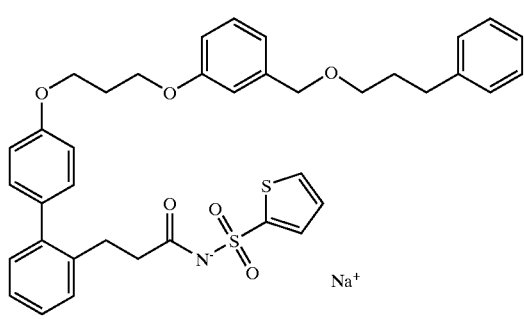
82
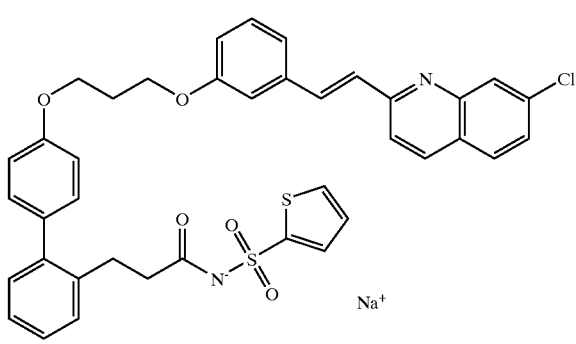
83
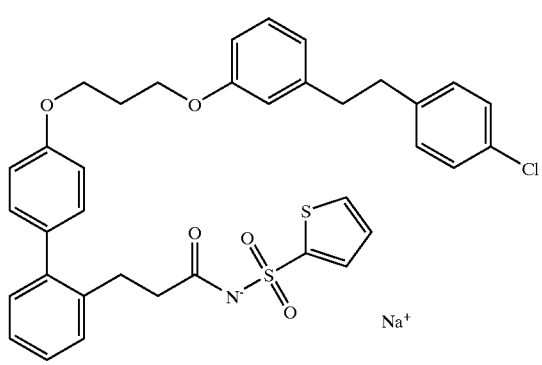
84
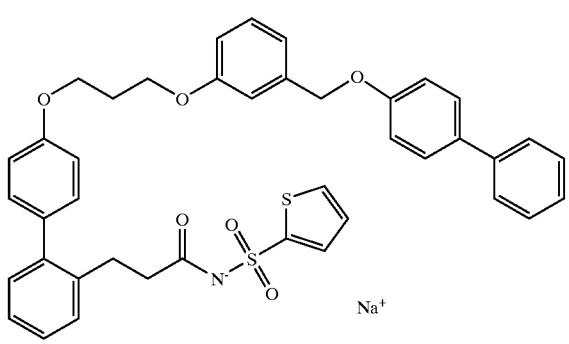
85
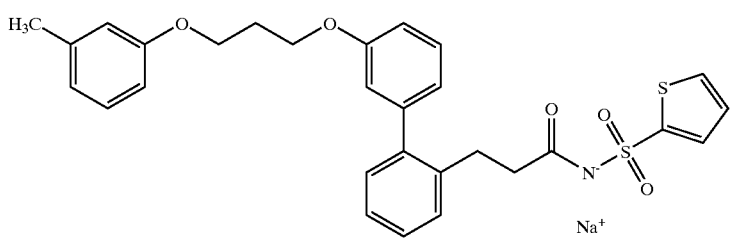
86
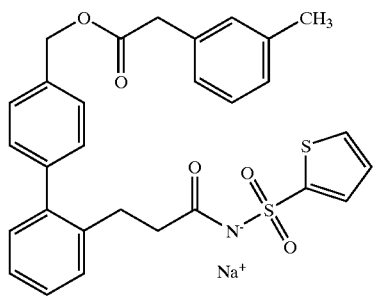
87
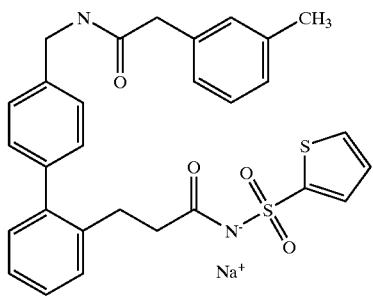
88
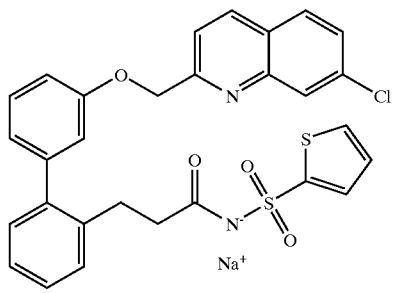
89
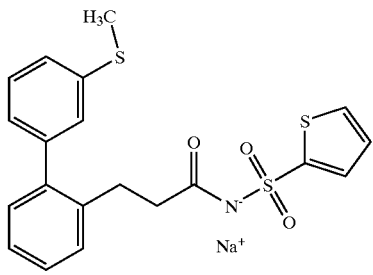
90

-continued
91
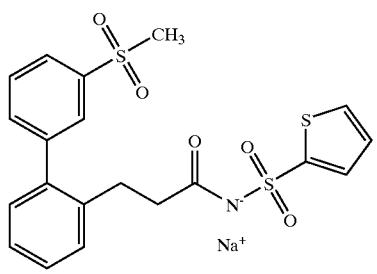
92
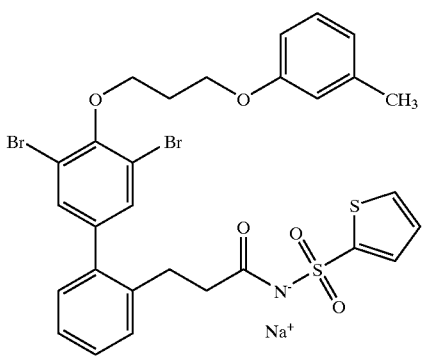
93
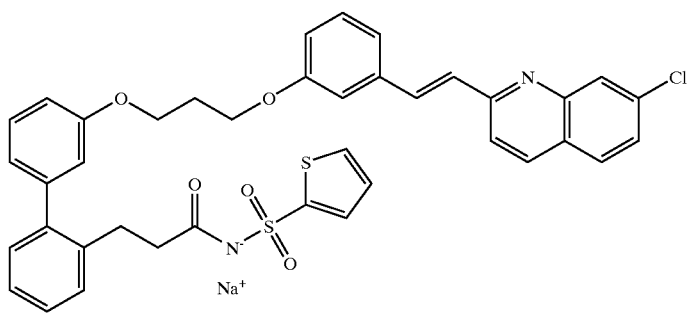
94
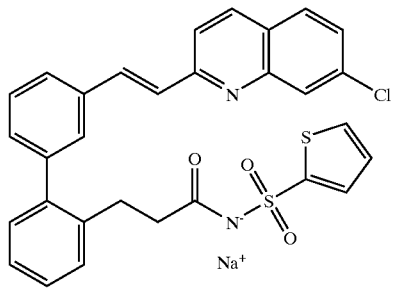
95
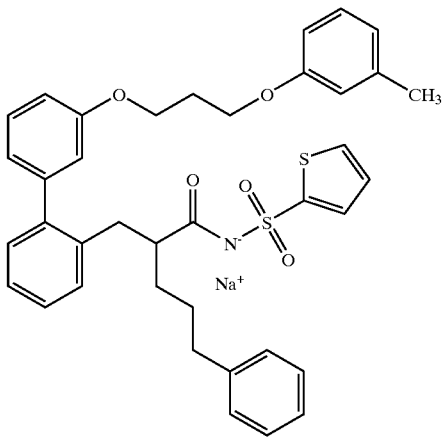
96
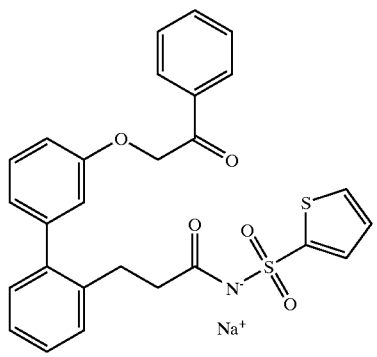
97
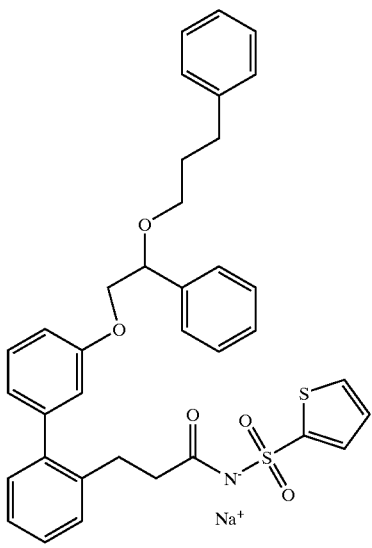

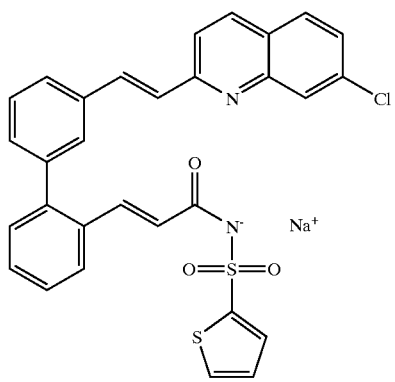

98

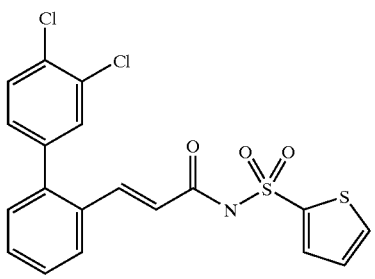

99

Definitions

The following abbreviations have the indicated meanings:
Ac=acetyl
AIBN=2,2'-azobisisobutyronitrile
Bn=benzyl
DIBAL=diisobutyl aluminum hydride
DIPHOS=1,2-bis(diphenylphosphino)ethane
DMAP=4-(dimethylamino)pyridine
DMF=N,N-dimethylformamide
DMSO=dimethyl sulfoxide
EDCI=1-(3-dimethylaminopropyl)-3-ethylcarbodiimide hydrochloride
$Et_3N$=triethylamine
EtOAc=ethyl acetate
HBBS=Hanks balanced salt solution
HEPES=N-[2-hydroxyethyl]piperazine-N'-[2-ethanesulfonic acid]
Hex=hexanes
KHMDS=potassium hexamethyldisilazane
LDA=lithium diisopropylamide
LPS=lipopolysaccharide
m-CPBA=metachloroperbenzoic acid
MES=2-[N-morpholino]ethanesulfonic acid
Ms=methanesulfonyl=mesyl
MsO=methanesulfonate=mesylate
NBS=N-bromosuccinimide
NSAID=non-steroidal anti-inflammatory drug
PCC=pyridinium chlorochromate
PDC=pyridinium dichromate
Ph=phenyl
PPTS=pyridinium p-toluenesulfonate
pTSA=p-toluenesulfonic acid
r.t.=room temperature
rac.=racemic
TLC=thin layer chromatography
Tf=trifluoromethanesulfonyl=triflyl
TfO=trifluoromethanesulfonate=triflate
THF=tetrahydrofuran
TLC=thin layer chromatography
Ts=p-toluenesulfonyl=tosyl
TsO=p-toluenesulfonate=tosylate
$C_3H_5$=allyl
Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl The terms alkyl, alkenyl, and alkynyl mean linear, branched, and cyclic structures and combinations thereof.

The term "alkyl" includes "cycloalkyl" and "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4-propylnonyl, and the like.

"Lower alkyl" includes "lower cycloalkyl" and means alkyl groups of from 1 to 7 carbon atoms. Examples of lower alkyl groups include methyl, ethyl, propyl, isopropyl, butyl, s- and t-butyl, pentyl, hexyl, heptyl, and the like.

"Cycloalkyl" includes "lower cycloalkyl" and means a hydrocarbon, containing one or more rings of from 3 to 12 carbon atoms, with the hydrocarbon having up to a total of 20 carbon atoms. Examples of cycloalkyl groups are cyclopropyl, cyclopentyl, cyclo-heptyl, aldamantyl, cyclododecylmethyl, $_2$-ethyl-1-bicyclo[4.4.0]decyl, and the like.

"Lower cycloalkyl" means a hydrocarbon containing one or more rings of from 3 to 7 carbon atoms, with the hydrocarbon having up to a total of 7 carbon atoms. Examples of lower cycloalkyl groups are cyclopropyl, cyclopropylmethyl, cyclobutyl, 2-cyclopentylethyl, cycloheptyl, bicyclo[2.2.1]hept-2-yl, and the like.

The term "alkenyl" includes "cycloalkenyl" and "lower alkenyl" and means alkenyl groups of 2 to 20 carbon atoms. Examples of alkenyl groups include allyl, 5-decen-1-yl, 2-dodecen-1-yl, and the like.

"Lower alkenyl" includes "lower cycloalkenyl" and means alkenyl groups of 2 to 7 carbon atoms. Examples of lower alkenyl groups include vinyl, allyl, isopropenyl, pentenyl, hexenyl, heptenyl, 1-propenyl, 2-butenyl, 2-methyl-2-butenyl, and the like.

"Cycloalkenyl" includes "lower cycloalkenyl" and means alkenyl groups of 3 to 20 carbon atoms, which include a ring of 3 to 12 carbon atoms, and in which the alkenyl double bond may be located anywhere in the structure. Examples of cycloalkenyl groups are cyclopropen-1-yl, cyclohexen-3-yl, 2-vinyladamant-1-yl, 5-methylene-dodec-1-yl, and the like.

"Lower cycloalkenyl" means alkenyl groups of 3 to 7 carbon atoms, which include a ring of 3 to 7 carbon atoms and in which the double bond may be located anywhere in the structure. Examples of lower cycloalkenyl groups are cyclopropen-1-yl, cyclohexen-3-yl, 2-cyclopentylethen-1-yl, and the like.

The term "alkynyl" includes "cycloalkynyl" and "lower alkynyl" and means alkynyl groups of 2 to 20 carbon atoms. Examples of alkynyl groups are ethynyl, 2-pentadecyn-1-yl, 1-eicosyn-1-yl, and the like.

"Lower alkynyl" includes "lower cycloalkynyl" and means alkynyl groups of 2 to 7 carbon atoms. Examples of lower alkynyl groups include ethynyl, propargyl, 3-methyl-1-pentynyl, 2-heptynyl and the like.

"Cycloalkynyl" includes "lower cycloalkynyl" and means alkynyl groups of 5 to 20 carbon atoms, which include a ring of 3 to 20 carbon atoms. The alkynyl triple bond may be located anywhere in the group, with the proviso that if it is within a ring, such a ring must be of 10 members or greater. Examples of cycloalkynyl are cyclododecyn-3-yl, 3-cyclohexyl-1-propyn-1-yl, and the like.

"Lower cycloalkynyl" means alkynyl groups of 5 to 7 carbon atoms which include a ring of 3 to 5 carbon atoms. Examples of lower cycloalkynyl are cyclopropylethynyl, 3-(cyclobutyl)-1-propynyl, and the like.

Halogen includes F, Cl, Br, and I.

It is intended that the definition of any substituent in a particular molecule be independent of its definition elsewhere in the molecule.

Optical Isomers—Diastereomers—Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromnic, hydrochloric, maleic, phosphoric, sulfuric, and tartaric acids.

It will be understood that in the discussion of methods of treatment which follows, references to the compounds of Formula I are meant to also include the pharmaceutically acceptable salts.

Dose Ranges

The magnitude of prophylactic or therapeutic dose of a compound of Formula I will, of course, vary with the nature and the severity of the condition to be treated and with the particular compound of Formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 2 g of an active ingredient, typically 25 mg, 50 mg, 100 mg, 200 mg, 300 mg, 400 mg, 500 mg, 600 mg, 800 mg, or 1000 mg.

Pharmaceutical Compositions

For the treatment of any of the prostanoid mediated diseases compounds of formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Utilities

The ability of the compounds of formula I to interact with prostaglandin receptors makes them useful for preventing or reversing undesirable symptoms caused by prostaglandins in a mammalian, especially human subject. This mimicking or antagonism of the actions of prostaglandins indicates that the compounds and pharmaceutical compositions thereof are useful to treat, prevent, or ameliorate in mammals and especially in humans: Pain, fever and inflammation of a variety of conditions including rheumatic fever, symptoms associated with influenza or other viral infections, common cold, low back and neck pain, skeletal pain, post-partum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures as well as immune and autoimmune diseases. In addition, such a compound may inhibit cellular neoplastic transformations and metastic tumor growth and hence can be used in the treatment of cancer. Compounds of formula I may also be of use in the treatment and/or prevention prostaglandin-mediated proliferation disorders such as may occur in diabetic retinopathy and tumor angiogenesis. Compounds of formula I will also inhibit prostanoid-induced smooth muscle contraction by antagonizing contractile prostanoids or mimicking relaxing prostanoids and hence may be use in the treatment of dysmenorrhea, premature labor, asthma and eosinophil related disorders. It will also be of use in the treatment of Alzheimer's disease, the treatment of glaucoma, for the prevention of bone loss (treatment of osteoporosis)

and for the promotion of bone formation (treatment of fractures) and other bone diseases such as Paget's disease.

By virtue of its prostanoid or prostanoid antagonist activity, a compound of formula I will prove useful as an alternative to conventional non-steroidal anti-inflammatory drugs (NSAID'S) particularly where such non-steroidal anti-inflammatory drugs may be contraindicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; thrombosis, occlusive vascular diseases; those prior to surgery or taking anti-coagulants. Compounds of formula I will also be useful as a cytoprotective agent for patients under chemotherapy.

Combinations with Other Drugs

Compounds of formula I will be useful as a partial or complete substitute for conventional antiinflammatory or analgesic compounds in preparations wherein they are presently co-administered with other agents or ingredients. Thus in further aspects, the invention encompasses pharmaceutical compositions for treating prostaglandin $E_2$ mediated diseases as defined above comprising a non-toxic therapeutically effective amount of the compound of formula I as defined above and one or more ingredients such as another pain reliever including acetaminophen or phenacetin; a COX-2 selective inhibiting agent; a conventional NSAID; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; another prostaglandin ligand including misoprostol, enprostil, rioprostil, ornoprostol or rosaprostol; a diuretic; a sedating or non-sedating antihistamine. In addition, the invention encompasses a method of treating prostaglandin $E_2$ mediated diseases comprising: administration to a patient in need of such treatment a non-toxic therapeutically effective amount of the compound of formula I, optionally co-administered with one or more of such ingredients as listed immediately above.

Methods of Synthesis

Compounds of the present invention can be prepared according to the general synthesis schemes appearing in WO96/30358, or in accordance with U.S. Pat. No. 5,391,817, incorporated herein by reference in its entirety. Alternativley, the compounds can be synthesized using the following methods:

Method A

This method make use of Z precursor containing protected acid unit (AC(O)B). Suzuki's cross coupling between excess aryl dihalide of type 1 and an appropriate boronic acid 2 led to the biaryl 3. In most cases, Pd(PPh$_3$)$_4$ is used as the catalyst, Na$_2$CO$_3$ or CsF as the base in a refluxing mixture of DME/H$_2$O (4/1). A second Suzuki's coupling between 3 and the boronate 4 followed by acidic hydrolysis of the resulting ester 5 (basic hydrolysis in the cases of methyl or ethyl ester) afforded the desired acid 6. A second strategy involves the formation of the boronic acid 7 from the corresponding halide 3 and a subsequent Suzuki's coupling with the aryl halide 8. Deprotection of the resulting ester 9 followed by coupling with an appropriate sulfonamide using EDCI/DMAP led to the acyl-sulfonamide 10.

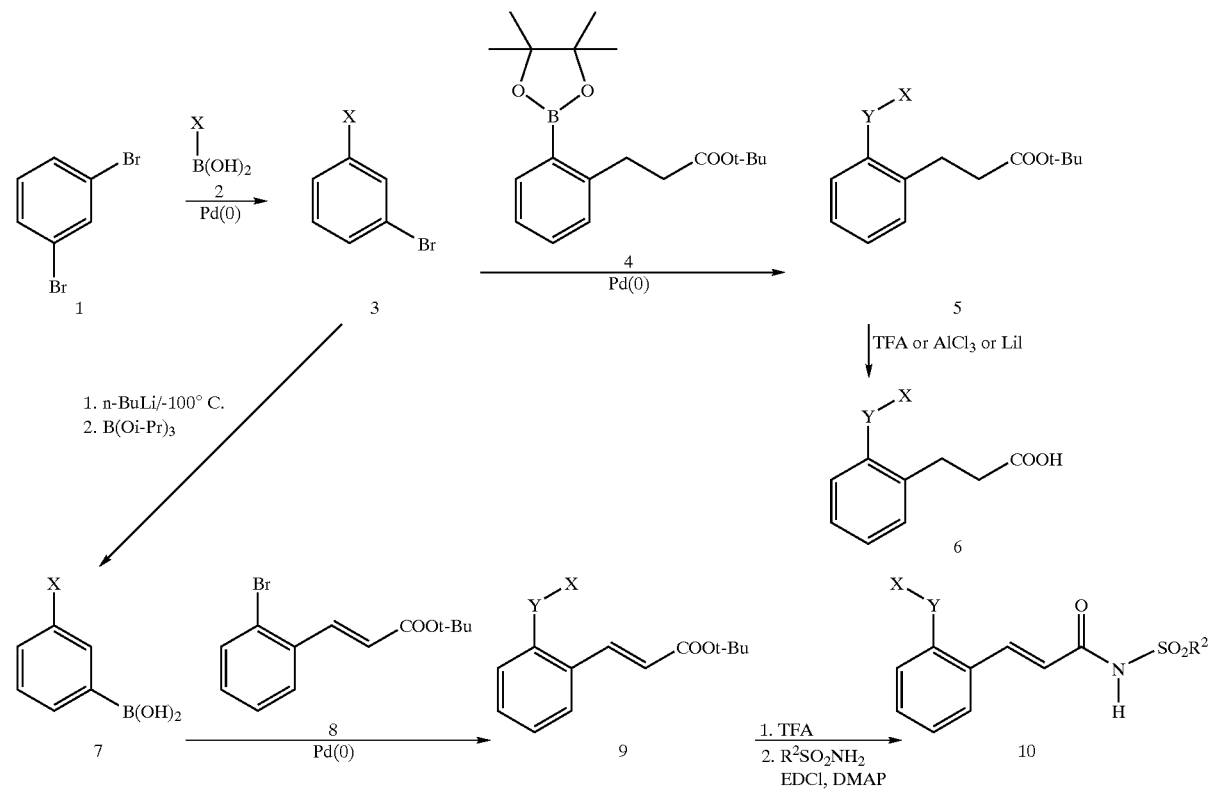

Method B

In this method the acid group (AC(O)B) is introduce by Horner-Emmons (or Wittig) condensation. Suzuki's coupling between the boronic acid 11 and the aryl dihalide 1 led to the aldehyde 12 under previously described conditions. The acid unit is introduce by a Horner-Emmons reaction to afford the diaryl halide 13 followed by cross coupling with the boronic acid 1 to give the desired ester 9. Alternatively, coupling between 12 and 2 followed by a Horner-Emmons reaction on the resulting aldehyde 14, can also afford the ester 9.

Method D

For the synthesis of compounds in which the central heteroaryl Y is a 2,4-thiazole or a 2,5-thiazole (21, 24) see the procedures described in the following references; Nan'ya, S.; Ishida, H.; Kanie, K; Ito, N.; Butsugan, Y. J. *Heterocyclic Chem.* 1995, 32, 1299. Zhang, M. Q.; Haemers, A.; Vanden Berghe, D.; Pattyn, S. R.; Bolaert, W. J. *Heterocyclic Chem.* 1991, 28, 673. Gordon, T. D.; Singh, J.; Hansen, P. E.; Morgan, P. A. *Tetrahedron Lett,* 1993, 34, 1901.

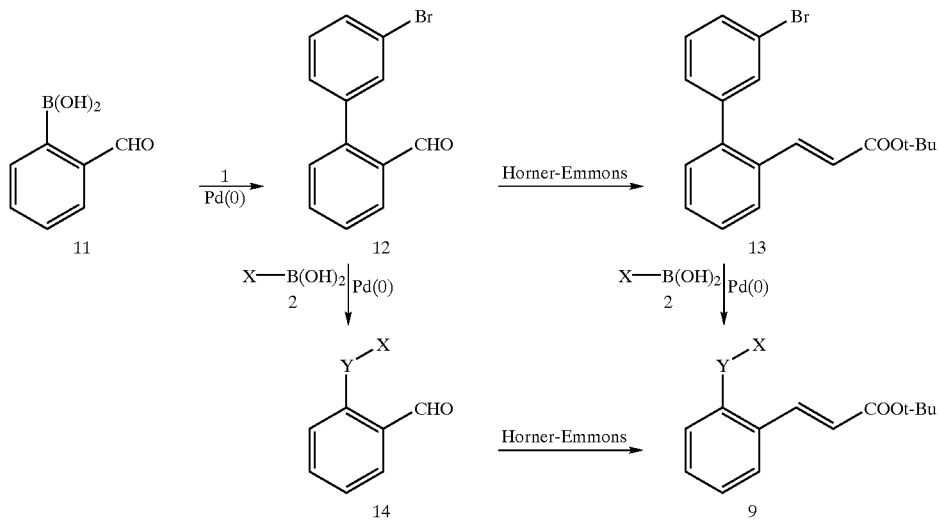

Method C

Upon addition of an alkylating reagent (R-Hal) to the anion of tert-butyl ester 15, generated in presence of a hindered base, monosubstituted (16) esters were obtained. The ester (16) can be further modified as described in method A to give the desired a-substituted acids 17.

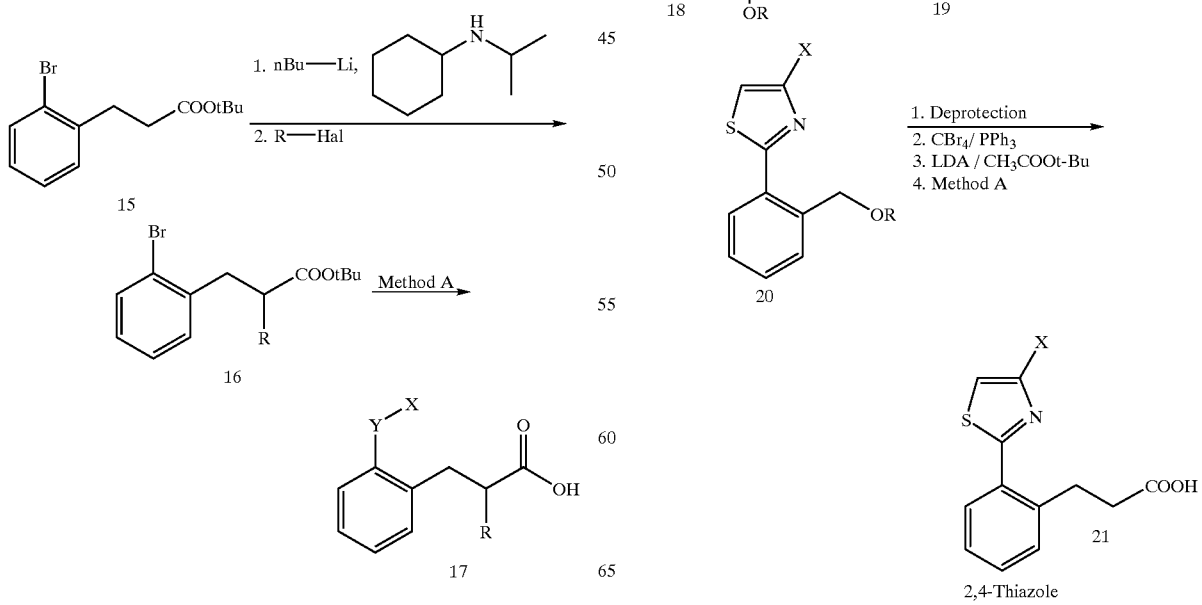

2,4-Thiazole

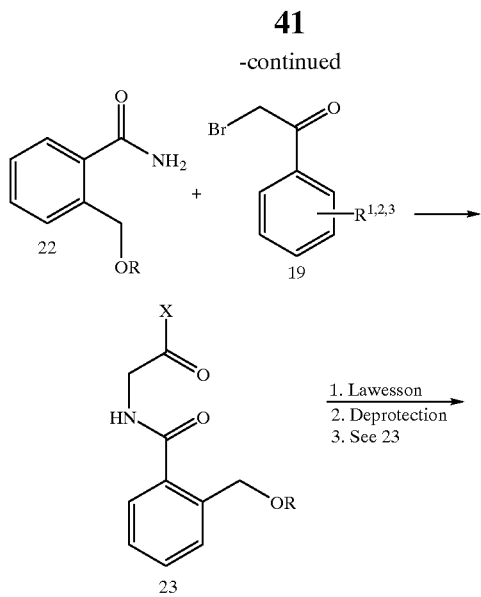

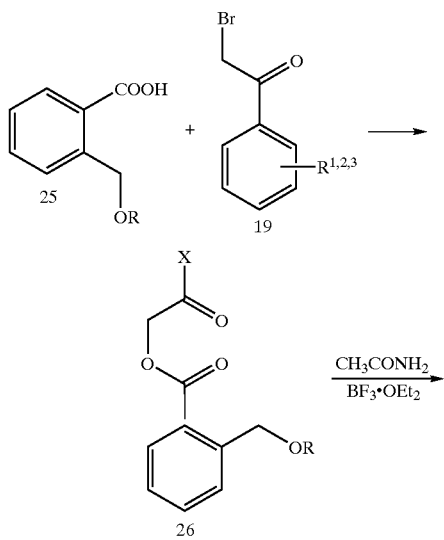

Method E

For the synthesis of compounds in which the central heteroaryl Y is a 2,4-oxazole or a 2,5-oxazole (28, 31) see the procedures described in the following references; Huang, W.; Pei, J.; Chen, B.; Pei, W.; Ye, X. *Tetrahedron*, 1996, 52, 10131. Hammar, W. J.; Rustad, M. A. *J. Heterocyclic Chem.* 1981, 18, 885.

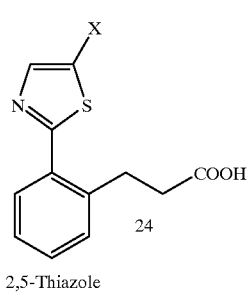

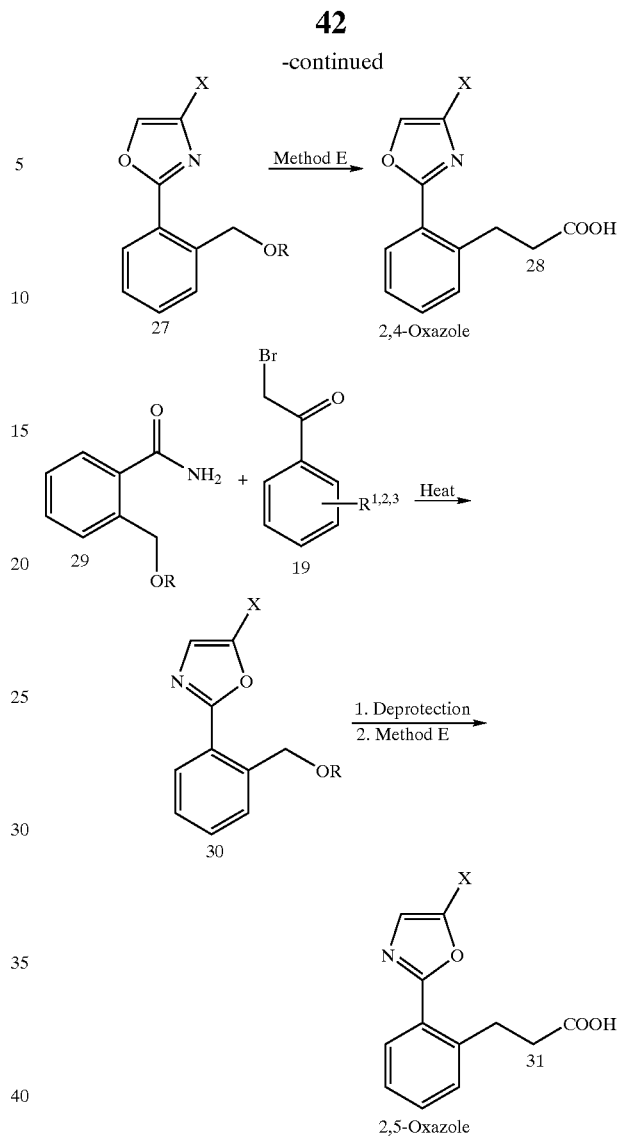

Method F

For the synthesis of compounds in which the central heteroaryl Y is a 4,1-imidazole (37) see the procedures described in the following references; Lopez-Alvarado, P.; Avendano, C.; Menendez, J. C. *J. Org. Chem.* 1995, 60, 5678. Horne, D. A.; Yakushijin, K.; Büchi, G. *Heterocycle* 1994, 39, 139. For the synthesis of aryllead triacetates see; Barton, D. H.; Finet, J. P.; Donnelly, D. M. X. *J. Chem. Soc. Perkin T.* 1 1992, 1365.

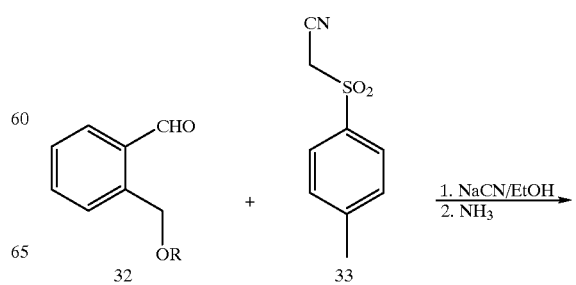

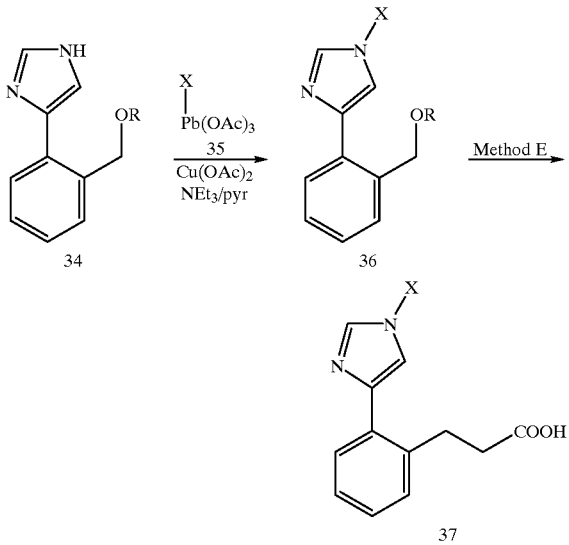

EXAMPLES

The species described herein can be made following the procedures set forth in the examples below, in which, unless otherwise stated:

The end products were analyzed by NMR, TLC and elementary analysis;

Intermediates were analyzed by NMR and TLC;

The compounds were purified by flash chromatography on silica gel, recrystallization and/or swish (suspension in a solvent followed by filtration of the solid);

The course of reactions was followed by thin layer chromatography (TLC) and reaction times are given for illustration only; and Some end products were converted to the sodium salt (dissolved in EtOH then addition of NaOH aq.)

The following intermediates were prepared according to literature procedures:

(Phenylmethoxy)benzeneboronic acid: Johnson, C. R.; Johns, B. A. *J. Org. Chem.* 1997, 62, 6046–6050.

2,4-Dibromo-5-chlorothiophene: Gronowitz, H. *Acta Chem. Scand.* Ser. B, 1976, 30, 439–445.

Lithium N-isopropylcyclohexylamnide; lithium tert-butyl acetyl: Paquette, L. A.; Ewing, G. D. *J. Org. Chem.* 1975, 40, 2965–2966.

Example 1

3-(2-{3-[5-Chloro-2-(phenylmethoxy)-3-pyridyl] phenyl}phenyl) propanoic acid (5)

Step 1; 2-(3-Bromophenyl)benzaldehyde

A mixture of 2-formylbenzeneboronic acid (15.35 g, 102 mmol), 1,3-dibromobenzene (75.25 g, 319 mmol), 2M $Na_2CO_3$ (150 mL) and $(Ph_3P)_4Pd$ (2.81 g, 24 mmol) in DME (600 mL) was heated to 80° C. for 4 h. The mixture was cooled to r.t., quenched with 1N HCl (or aqueous $NH_4Cl$) and extracted with EtOAc. The organic layer was washed with brine, dried ($MgSO_4$), filtered and concentrated. Purification by flash chromatography (Tol:Hex, 0:1 to 1:1) provided the desired material as a yellow solid (21.3 g, 80%). $^1$H NMR (acetone-$d_6$) δ 7.4–7.8 (7H, m), 7.97 (1H, ddd), 9.95 (1H, s).

Step 2; Ethyl (E)-3-[2-(3-bromophenyl)phenyl]prop-2-enoate

To 2-(3-bromophenyl)benzaldehyde (6.67 g, 25.5 mmol) and triethyl phosphonoacetate (6.89 g, 30.7 mmol) in Tol (90 mL) at 0° C. was added NaH (38.7 mmol). The reaction mixture was stirred at r.t. overnight. The reaction mixture was poured into aqueous $NH_4Cl$ and extracted twice with $Et_2O$. The combined organic extracts were washed ($H_2O$:brine), dried ($MgSO_4$), filtered and concentrated. Purification by flash chromatography (Tol) afforded the desired material as a colorless oil (8.01 g, 95%). $^1$H NMR (acetone-$d_6$) δ 1.25 (3H, t), 4.16 ($_2$H, q), 6.50 (1H, d), 7.3–7.7 (8H, m), 7.89 (1H, m).

Step 3; (E)-3-[2-(3-bromophenyl)phenyl]prop-2-enoic acid

The previous ester (8.01 g, 24.2 mmol) was hydrolyzed in THF:MeOH:2N LiOH (80 mL :40 mL :40 mL). After being stirred at r.t. overnight, the reaction mixture was poured into 1N HCl (or $H_2O$:AcOH 10%) and extracted with EtOAc. The organic layer was washed with brine, dried ($MgSO_4$), filtered and concentrated. Purification by a swish (Hex:EtOAc, 1:1) provided the title compound as a white crystalline solid (6.33 g, 86%). $^1$H NMR (acetone-$d_6$) δ 6.49 (1H, d), 7.3–7.7 (8H, m), 7.90 (1H, m).

Step 4; 3-[2-(3-Bromophenyl)phenyl]propanoic acid

To the previous acid (7.19 g, 23.7 mmol) suspended in EtOAc (125 mL) was added $PtO_2$ (262 mg, 1.14 mmol). After being sonicated for 2 h and stirred at r.t. for 2 days under a hydrogen atmosphere, the suspension was filtered over Celite and concentrated. Purification by a swish (Hex) afforded the title compound as a white solid (6.27 g, 86%). $^1$H NMR (acetone-$d_6$) δ 2.46 (2H, t), 2.88 (2H, t), 7.18 (1H, dd), 7.28 (1H, td), 7.3–7.4 (4H, m), 7.52 (1H, t), 7.56 (1H, ddd).

Step 5; Methyl 3-{2-[3-(4,4,5,5-tetramethyl-1,3,2-dioxaborolan-2-yl)phenyl]phenyl}propanoate After esterification of the previous acid (1.72 g, 5.64 mmol) in ether (20 mL) with an excess of diazomethane at 0° C., the solution was dried ($MgSO_4$), filtered and concentrated. To this crude ester in DMF (20 mL), diboron pinacol ester (1.57 g, 6.20 mmol), $PdCl_2$(dppf) (138 mg, 0.169 mmol) and KOAc (1.78 g, 18.14 mmol) were added. After heating at 80° C. for 2 h, the mixture was poured into water and extracted twice with $Et_2O$. The combined organic extracts were washed ($H_2O$:brine), dried ($MgSO_4$), filtered and concentrated. Purification by flash chromatography (Tol:Hex:EtOAc, 1:0:0 to 0:4:1) afforded the desired material as a yellow oil (1.42 g, 69%). $^1$H NMR (acetone-$d_6$) δ 1.33 (12H, s), 2.45 (2H, t), 2.89 (2H, t), 3.54 (3H, s), 7.18 (1H, dd), 7.2–7.4 (3H, m), 7.46 (2H, m), 6.67 (1H, m), 7.75 (1H, m).

Step 6; 3-Bromo-5-chloro-2-(phenylmethoxy)pyridine

A mixture of 3-bromo-5-chloropyridin-2-ol (50 g, 242 mmol), benzyl bromide (32 mL, 269 mmol) and $Ag_2CO_3$ (60 g, 218 mmol) in benzene (500 mL) was refluxed for 1 h. The suspension was filtered over Celite and concentrated. The crude material was put under vacuo overnight to obtain the title compound as a yellow solid. $^1$H NMR (acetone-$d_6$) δ 5.44 (2H, s), 7.2–7.4 (3H, m), 7.50 (2H, m), 8.07 (1H, d) 8.16 (1H, d).

Step 7; Methyl 3-(2-{3-[5-chloro-2-(phenylmethoxy)-3-pyridyl]phenyl}phenyl) propanoate A mixture of methyl ester (404 mg, 1.10 mmol) of step 5 in this example, 3-bromo-5-chloro-2-(phenylmethoxy) pyridine (650 mg, 2.18 mmol), $PdCl_2$(dppf) (33 mg, 0.04 mmol) and 2M $Na_2CO_3$ (2.4 mL) in DMF (6 mL) was heated to 80° C. overnight. The mixture was quenched with 1N HCl and extracted twice with $Et_2O$. The combined organic extracts were washed ($H_2O$:brine), dried ($MgSO_4$), filtered and concentrated. Purification by flash chromatography (Tol) afforded the desired material as a white solid (394 mg, 78%). ¹H NMR (acetone-$d_6$) δ 2.41 (2H, t), 2.89 (2H, t), 3.50 (3H, s), 5.45 (2H, s), 7.15 (1H, dd), 7.2–7.5 (9H, m), 7.52 (1H, dd), 7.6–7.7 (2H, m), 7.88 (1H, d), 8.16 (1H, d).
Step 8; 3-(2-{3-[5-Chloro-2-(phenylmethoxy)-3-pyridyl] phenyl}phenyl)propanoic acid As described in Example 1 (step 3), the previous ester (394 mg, 0.86 mmol) was hydrolyzed in THF:MeOH:2N LiOH (4 mL:2 mL:2 mL). Purification by a swish (Hex:EtOAc) afforded the title compound as a white solid (360 mg, 94%). ¹H NMR (acetone-$d_6$) δ 2.42 (2H, t), 2.91 (2H, t), 5.45 (2H, s), 7.16 (1H, dd), 7.2–7.4 (9H, m), 7.52 (1H, td), 7.6–7.7 (2H, m), 7.89 (1H, d), 8.16 (1H, d).

Example 2

(E)-3-(2-{3-[2-(Phenylmethxoy)phenyl] phenyl}phenyl) prop-2-enoic acid (7)

Step 1: Ethyl (E)-3-(2-{3-[2-(phenylmethoxy)phenyl] phenyl}phenyl)prop-2-enoate

As described in Example 1 (step 1), a mixture of 2-(phenylmethoxy) benzeneboronic acid (545 mg, 2.39 mmol), ethyl (E)-3-[2-(3-bromophenyl)phenyl]prop-2-enoate bromide (390 mg, 1.18 mmol) of Example 1 (step 2), 2M $Na_2CO_3$ (3.5 mL) and $(Ph_3P)_4Pd$ (66 mg, 0.06 mmol) in DME (7 mL) was heated to 80° C. for 2 h. Purification by flash chromatography (Tol) provided the desired material as a yellow solid (485 mg, 95%). ¹H NMR (acetone-$d_6$) δ 2.04 (3H, t), 4.12 (2H, q), 5.16 (2H, s), 6.51 (1H, d), 7.07 (1H, td), 7.20 (1H, dd), 7.2–7.4 (8H, m), 7.4–7.5 (4H, m), 7.6–7.7 (2H, m), 7.79 (1H, d) and 7.89 (1H, dd).
Step 2: (E)-3-(2-{3-[2-(Phenylmethoxy)phenyl] phenyl}phenyl)prop-2-enoic acid The previous ester (483 mg, 1.11 mmol) was hydrolyzed in THF:MeOH:2N LiOH (4 mL:2 mL:2 mL) at 50° C. for 1 h. Purification by a swish (Hex:$Et_2O$) afforded the desired material as a white solid (419 mg, 93%). ¹H NMR (acetone-$d_6$) δ 5.15 (2H, s), 6.49 (1H, d), 7.05 (1H, td), 7.20 (1H, dd), 7.2–7.4 (8H, m), 7.4–7.5 (4H, m), 7.60 (2H, m), 7.80 (1H, d) and 7.89 (1H, dd).

Example 3

(E)-3-(2-{5-[2-(Phenylmethoxy)phenyl]-3-pyridyl}phenyl) prop-2-enoic acid (8)

Step 1; 2-(5-Bromo-3-pyridyl)benzaldehyde

As described in Example 1 (step 1), a mixture of 2-formylbenzeneboronic acid (2.00 g, 13.3 mmol), 3,5-dibromopyridine (9.52 g, 40.2 mmol), 2M $Na_2CO_3$ (17 mL) and $(Ph_3P)_4Pd$ (762 mg, 0.66 mmol) in DME (80 mL) was heated to 80° C. for 12 h. Purification by flash chromatography (Tol:EtOAc, 1:0 to 19:1) provided the desired material as a yellow oil (2.85 g, 82%). ¹H NMR (acetone-$d_6$) δ 7.56 (1H, m), 7.68 (1H, t), 7.79 (1H, td), 8.03 (1H, dd), 8.11 (1H, t), 8.60 (1H, d), 8.74 (1H, d), 10.01 (1H, s).
Step 2; 2-{5-[2-(Phenylmethoxy)phenyl]-3-pyridyl}benzaldehyde As described in Example 1 (step 1), a mixture of the previous bromide (507 mg, 1.93 mmol, step 1), 2-(phenylmethoxy)benzeneboronic acid (638 mg, 2.80 mmol), 2M $Na_2CO_3$ (3.5 mL) and $(Ph_3P)_4Pd$ (102 mg, 0.09 mmol) in DME (10 mL) was heated to 80° C. for 6 h. Purification by flash chromatography (Tol:EtOAc, 9:1) provided the desired material as a yellow oil (642 mg, 91%). ¹H NMR (acetone-$d_6$) δ 5.19 (2H, s), 7.1–7.4 (9H, m), 7.51 (1H, dd), 7.63 (1H, t), 7.74 (1H, td), 8.01 (1H, dd), 8.06 (1H, t), 8.55 (1H, d), 8.83 (1H, d), 10.03 (1H, s).
Step 3; (E)-3-(2-{5-[2-(Phenylmethoxy)phenyl]-3-pyridyl}phenyl)prop-2-enoic acid As described in Example 1 (step 2), a mixture of the previous aldehyde (640 mg, 1.75 mmol, step 2), triethyl phosphonoacetate (420 uL, 2.12 mmol) and NaH (2.7 mmol) in Tol (6 mL) was stirred at rt for 6 h. The crude material was not purified. According to the procedure described in step 8 of Example 1, the crude ester was hydrolyzed in THF:MeOH:2N LiOH (6 mL:3 mL:3 mL). Purification by a swish (Hex:EtOAc) afforded the desired material as a white solid (641 mg, 90%). ¹H NMR (acetone-$d_6$) δ 5.15 (2H, s), 6.52 (1H, d), 7.09 (1H, t), 7.2–7.4 (7H, m), 7.42 (1H, m), 7.50 (4H, m), 7.94 (2H,m), 8.42 (1H,d) 8.78 (1H, d).

Example 4

(E)-3-(2-{3-[2-(Phenylmethoxy)phenyl] phenyl}phenyl)-N-(2-thienylsulfonyl)prop-2-enamide (55)

To (E)-3-(2-{3-[2-(Phenylmethoxy)phenyl] phenyl}phenyl)prop-2-enoic acid (210 mg, 0.52 mmol) of Example 2 (step 2), 2-thiophenesulfonylamide (121 mg, 0.74 mmol) and DMAP (250 mg, 2.04 mmol) in $CH_2Cl_2$ (3 mL) was added EDCI (142 mg, 0.74 mmol). After stirring at r.t. for 2 days, the reaction mixture was poured into 1N HCl (or aqueous AcOH) and extracted with EtOAc. The organic layer was washed with brine, dried ($MgSO_4$), filtered and concentrated. Purification by flash chromatography (Tol:EtOAc:AcOH, 1:0:0 to 20:1:0.1) and recrystallization (Hex:$CH_2Cl_2$) provided the desired material as a white solid (161 mg, 56%). ¹H NMR (acetone-$d_6$) δ 5.13 (2H, s), 6.72 (1H, d), 7.04 (1H, td), 7.1–7.2 (2H, m), 7.2–7.4 (8H, m), 7.4–7.5 (4H, m), 7.55 (1H, t), 7.62 (1H, dt), 7.7–7.8 (3H, m) and 7.92 (1H, dd).

Example 5

2-Methyl-3-(2-{4-[3-(3-methylphenoxy)propoxy] phenyl}phenyl)-N-(2-thienylsulfonyl)propanamide (84)

Step 1; 3-(4-Bromophenoxy)propan-1-ol

To 4-bromo phenol (151 g; 0.87 mol) and 3-bromo propanol (120 mL; 1.3 mol) in 1.2 L of acetone was added portionwise $K_2CO_3$ (152 g; 1.1 mol). Final mixture was refluxed for 12 h, cool to rt, filtered and concentrated. Distillation (0.2 mm Hg; 120° C.) afforded the desired material as a colorless oil (173 g; 86%). ¹H NMR (acetone-$d_6$) δ 1.95 (2H, m), 3.58 (1H, t), 3.67 (2H, m), 4.08 (2H, t), 6.90 (2H, d), 7.41 (2H, d).
Step 2; 1-Bromo-4-[3-(3-methylphenoxy)propoxy]benzene To a solution of the previous alcohol (10.1 g; 44 mmol) in 110 mL of $CH_2Cl_2$ at −50° C. was added $NEt_3$ (9.0 mL; 65 mmol) then dropwise MsCl (4.0 mL; 52 mmol). Final mixture was allowed to reach 0° C. then poured in saturated aqueous $NaHCO_3$ and extracted with $CH_2Cl_2$ (2×). The combined organic extracts were dried over, filtered and concentrated to afford the mesylate, which was used without further purification. To a solution of m-cresol (6.6 g; 61 mmol) in 130 mL of DMF was added portionwise NaH (1.6 g; 80%; 52 mmol). The mixture was stirred 1 h at rt then the mesylate was added. Final mixture was stirred 12 h at rt then was poured in $H_2O$ and extracted with $Et_2O$ (3×). The combined organic extracts were washed with $H_2O$ (2×), brine, dried over $MgSO_4$, filtered and concentrated. The excess m-cresol was removed by basic extraction (NaOH 1n; Hex) to afford the title compound as a white solid (13.5 g; 96%). ¹H NMR (acetone-$d_6$) δ 2.22 (2H, m), 2.27 (3H, s), 4.17 (4H, m), 6.74 (3H, m), 6.92 (2H, dd), 7.13 (1H, t), 7.41 (2H, dd).

Step 3; Tert-butyl 3-(2-{4-[3-(3-methylphenoxy)propoxy] phenyl}phenyl)propanoate To a solution of the previous aryl bromide (6.16 g; 19.1 mmol) in 70 mL of DME at −78° C. was added dropwise n-BuLi (8.4 mL; 2.5 M; 21 mmol). After stirring 30 min at −78° C., triiso-propyl boronate (4.4 mL; 19.1 mmol) was added and the solution was warmed to rt and stirred for 2 h. To this solution of boronate was added $Na_2CO_3$ (28 mL; 2 M; 56 mmol), Tert-butyl 3-(2-bromophenyl)propanoate (Example 4; step 1; 4.19 g; 14.7 mmol) and $Pd(PPh_3)_4$ (0.27 g; 0.24 mmol). The final mixture was stirred at 85° C. for 6 h then was poured in HCl (1N) and extracted with EtOAc (2×). The combined organic extracts were washed brine, dried over $Na_2SO_4$, filtered and concentrated. Flash chromatography (Hex:EtOAc; 7:3) yielded the title compound as a yellow oil (6.69 g; 78%). $^1$H NMR (acetone-$d_6$) δ 6 1.33 (9H, s), 2.25–2.35 (7H, m), 2.87 (2H, t), 4.15–4.25 (4H, m), 6.76 (3H, m), 7.03 (2H, dd), 7.15 (2H, m), 7.2–7.3 (5H, m).

Step 4; Tert-butyl 2-methyl-3-(2-{4-[3-(3-methylphenoxy) propoxy]phenyl}phenyl)propanoate A solution of the previous ester (2.76 g, 6.17 mmol) in THF (10 mL) was added to a solution of lithium N-isopropylcyclohexylamide (56 mL; 0.14 M; 7.8 mmol) in THF at −78° C. then 30 min later, iodomethane (1.3 mL, 21 mmol). The solution was warmed slowly (1.5 h) at 0° C., then poured in 1N HCl and extracted with EtOAc (2×). The combined organic extracts were washed with brine, dried over $MgSO_4$, filtered and concentrated. Flash chromatography (Hex:EtOAc; 7:3) afforded the title compound as a yellow oil (2.47 g; 86%). $^1$H NMR (acetone-$d_6$) δ 0.88 (3H, d), 1.27 (9H, s), 2.2–2.4 (6H, m), 2.68 (1H, dd), 2.93 (1H, dd), 4.20 (2H, t), 4.24 (2H, t), 6.76 (3H, m), 7.03 (2H, dd), 7.15 (2H, m), 7.24 (5H, m).

Step 5: 2-methyl-3-(2-{4-[3-(3-methylphenoxy)propoxy] phenyl}phenyl)propanoic acid To a solution of the previous ester (1.33 g; 2.88 mmol) in 9 mL of $CH_2Cl_2$ at 0° C. was added TFA (4.5 mL; 58 mmol). The resulting solution was stirred at rt until all starting material was consumed as monitored by TLC. Two co-evaporation with Tol followed by flash chromatography (Tol:EtOAc:AcOH; 10:0.5:0.05) afforded the desired acid as a colorless oil (1.04 g; 89%). $^1$H NMR (acetone-$d_6$) δ 0.92 (3H, d), 2.27 (5H, m), 2.52 (1H, m), 2.69 (1H, dd), 3.05 (1H, dd), 4.20 (2H, t), 4.24 (2H, t), 6.76 (3H, m), 7.02 (2H, dd), 7.1–7.3 (7H, m).

Step 6 2-Methyl-3-(2-{4-[3-(3-methylphenoxy)propoxy] phenyl}phenyl)-N-(2-thienyl sulfonyl)propanamide To a solution of the previous acid (453 mg; 1.12 mmol) in 10 mL of $CH_2Cl_2$ at 0° C. was added oxalyl chloride (0.30 mL; 3.3 mmol) then a catalytic amount of DMF (35 µL). The resulting solution was stirred at rt was monitored by MeOH quench/TLC. Two co-evaporation with Tol afforded the desired acid chloride, which was used without any further purification. The acid chloride was dissolved in 7 mL of $CH_2Cl_2$, cooled to 0° C., then DIPEA (580 mL; 3.3 mmol) and and 2-thiophenesulfonylamide (222 mg, 1.4 mmol) were added simultaneously. The resulting solution was stirred at rt for 12 h, quenched with 25 mL MeOH, concentrated, poured in $H_2O$ (10% AcOH) and extracted with EtOAc (2×). The combined organic extracts were washed brine, dried over $Na_2SO_4$, filtered and concentrated. Flash chromatography ($CH_2Cl_2$:MeOH 2.5%) afforded the title compound (350 mg; 56%). The carboxylic acid was converted to it's corresponding sodium salt (EtOH: NaOH 1N). $^1$H NMR (acetone-$d_6$) δ 0.93 (3H, d), 2.27 (5H, m), 2.60–2.75 (2H, m), 2.91 (1H, dd), 4.22 (4H, m), 6.77 (3H, m), 7.01 (2H, d), 7.05–7.25 (8H, m), 7.74 (1H, dd), 7.94 (1H, dd).

Example 6

(E)-3-{2-[3-(3-{3-[2-(7-Chloro(2-quinolyl))vinyl] phenoxy}propoxy)phenyl]phenyl}-N-(2-thienylsulfonyl)propanamide (98)

Step 1: 3-(3-Bromophenoxy)propan-1-ol

Prepared as described in Example 5 (step 1) from 3-bromo phenol. $^1$H NMR (acetone-$d_6$) δ 1.95 (2H, m), 3.69 (3H, m), 4.12 (2H, t), 6.93 (1H, dd), 7.08 (2H, m), 7.23 (1H, t).

Step 2: {3-[3-(3-Bromophenoxy)propoxy]phenyl}methan-1-ol

Prepared as described in Example 5 (step 2) from the corresponding mesylate of the previous alcohol and 3-hydroxymethyl phenol. $^1$H NMR (acetone-$d_6$) δ 2.23 (2H, quint.), 4.18 (5H, m), 4.59 (2H, d), 6.81 (1H, dd), 6.90 (1H, d), 6.96 (2H, m), 7.05–7.25 (4H, m).

Step 3; 3-{3-[3-(Hydroxymethyl)phenoxy] propoxy}benzeneboronic acid

To a solution of the previous aryl bromide (15.6 g; 46 mmol) in 200 mL of THF at −78° C. was added dropwise n-BuLi (40 mL; 2.5 M; 100 mmol). After stirring 45 min at −78° C., triiso-propyl boronate (27 mL; 116 mmol) was added, the solution was warmed to rt and stirred for 9 h. HCl (1N) was added until the pH=1, the resulting mixture was diluted with $H_2O$ and extracted with EtOAc. The organic extract was washed with $H_2O$ (2×), brine, dried over $Na_2SO_4$, filtered and concentrated. Purification by swish (Hex:EtOAc:$H_2O$) yielded the title compound as a white solid (5.3 g; 38%). $^1$H NMR (acetone-$d_6$) δ

Step 4: Tert-butyl 3-[2-(3-{3-[3-(hydroxymethyl)phenoxy] propoxy}phenyl)phenyl]propanoate The previous boronic acid (5.26 g; 17.4 mmol), tert-butyl 3-(2-bromophenyl) propanoate (5.99 g; 21 mmol), $Pd(PPh_3)_4$ (1.21 g; 1.1 mmol) and $Na_2CO_3$ (20 mL; 2 N; 40 mmol) were combined in 100 mL of DME. Nitrogen was bubbled in the suspension for 15 min then it was stirred at 80° C. for 8 h. The mixture was cooled to rt, poured in saturated aqueous $NH_4Cl$ then extracted with EtOAc (2×). The combined organic extracts were dried over $Na_2SO_4$, filtered and concentrated. Flash chromatography (Tol:EtOAc; 90:10) afforded the title compound (5.18 g; 64%). $^1$H NMR (acetone-$d_6$) δ 1.33 (9H, s), 2.26 (2H, m), 2.34 (2H, m), 2.88 (2H, t), 4.09 (1H, t), 4.20 (2H, t), 4.25 (2H, t), 4.58 (2H, d), 6.81 (1H, dd), 6.85–7.00 (5H, m), 7.1–7.4 (6H, m).

Step 5; Tert-butyl 3-(2-{3-[3-(3-formylphenoxy)propoxy] phenyl}phenyl)propanoate To a solution of the previous benzyl alcohol (5.18 g; 11.2 mmol) in 75 mL of EtOAc at 0° C. was added $MnO_2$ (30.2 g; 0.34 mol) portionwise. The suspension was stirred at rt for 4 h, filtered on Celite, and concentrated to yield the title compound (4.30 g; 84%). %). $^1$H NMR (acetone-$d_6$) δ 1.33 (9H, s), 2.32 (4H, m), 2.87 (2H, t), 4.29 (4H, m), 6.90 (2H, m), 6.98 (1H, m), 7.17 (1H, m), 7.2–7.4 (5H, m), 7.49 (3H, m), 9.99 (1H, s).

Step 6; Tert-butyl (E)-3-{2-[3-(3-{3-[2-(7-chloro-2-guinolyl)vinyl]phenoxy}propoxy) phenyl] phenyl}propanoate To a suspension of (7-chloroquinolin-2-yl)methyl triphenylphosphonium bromide (1.71 g; 3.3 mmol) in 15 mL THF at −78° C. was added dropwise t-BuOK (3.6 mL; 1.0 M; 3.6 mmol). The mixture was stirred at −78° C. for 15 min, at 0° C. for 30 min then was cooled down to −78° C. A solution of the previously described aldehyde (1.04 g; 2.3 mmol) in 3 mL THF was cannulated and the final mixture was stirred 5 h at 0° C. It was poured in $H_2O$: AcOH 10% and extracted with EtOAc (2×). The combined organic extracts were dried over Na$_2$SO$_4$, filtered and concentrated. Flash chromatography (Tol then Tol:EtOAc; 95:5) afforded the title compound (1.39 g; 98%). $^1$H NMR (acetone-d$_6$) δ 1.32 (9H, s), 2.32 (4H, m), 2.88 (2H, t), 4.29 (4H, q), 6.85–7.00 (4H, m), 7.1–7.4 (8H, m), 7.44 (1H, d), 7.51 (1H, dd), 7.79 (1H, d), 7.85 (1H, d), 7.92 (1H, d), 7.99 (1H, dd), 8.30 (1H, d).

Step 7: (E)-3-{2-[3-(3-{3-[2-(7-chloro-2-quinolyl)vinyl]phenoxy}propoxy) phenyl]phenyl}propanoic acid To a solution of the previous ester (1.39 g; 2.24 mmol) in 60 mL of Tol was added AlCl$_3$ (0.90 g; 6.76 mmol). The suspension was stirred for 12 h, poured in H$_2$O and extracted with EtOAc (2×). The combined organic extracts were washed with brine, dried over Na$_2$SO$_4$, filtered and concentrated. Flash chromatography (Tol:EtOAc:AcOH; 95:5:1) afforded the title compound (894 mg; 71%). $^1$H NMR (acetone-d$_6$) δ 2.28 (2H, m), 2.48 (2H, m), 2.94 (2H, t), 4.28 (4H, m), 6.90 (1H, m), 6.97 (3H, m), 7.1–7.4 (8H, m), 7.50 (2H, m), 7.82 (2H, m), 7.90 (1H, d), 8.02 (1H, d), 8.28 (1H, d).

Step 8: (E)-3-{2-[3-(3-{3-[2-(7-chloro(2-quinolyl))vinyl]phenoxy }propoxy)phenyl]phenyl}-N-(2-thienylsulfonyl)propanamide To a mixture of the previous acid (696 mg; 1.23 mmol), 2-thiophenesulfonylamide (404 mg; 2.48 mmol) and DMAP (233 mg; 1.91 mmol) in 6 mL of CH$_2$Cl$_2$ was added EDCI (358 mg; 1.87 mmol). The mixture was stirred at rt for 12 h, poured in saturated aqueous NH4Cl and extracted with CH$_2$Cl$_2$ (2×). The combined organic extracts were dried over Na$_2$SO$_4$, filtered and concentrated. Flash chromatography (Tol:EtOAc:AcOH; 95:5:1) afforded the title compound (614 mg; 75%). $^1$H NMR (acetone-d$_6$) δ 2.28 (2H, m), 2.55 (2H, t), 2.88 (2H, t), 4.26 (4H, q), 6.83 (1H, m), 6.88 (1H, m), 6.95 (2H, m), 7.10–7.35 (9H, m), 7.44 (1H, d), 7.49 (1H, dd), 7.75–7.90 (5H, m), 8.00 (1H, d), 8.26 (1H, d).

Example 7

(E)-3-(2-{3-[2-(7-Chloro(2-quinolyl))vinyl]phenyl}phenyl)-N-(2-thienylsulfonyl)prop-2-enamide (103)

Step 1: (E)-2-{3-[2-(7-chloro-2-quinolyl)vinyl]phenyl}benzaldehyde

Prepared as described in Example 1 (step 1) from (E)-2-[2-(3-bromophenyl)vinyl]-7-chloroquinoline (prepared as described Example 8 (step 6), from 3-bromobenzaldehyde) and 2-formyl benzeneboronic acid (1.5 eq.). Title compound was purified by swish (Hex: CH$_2$Cl$_2$). $^1$H NMR (CDCl$_3$) δ 7.3–7.6 (6H, m), 7.6–7.8 (6H, m), 8.0–8.1 (3H, m), 10.03 (1H, d).

Step 2: Ethyl (E)-3-(2-{3-[2-(7-chloro-2-quinolyl)vinyl]phenyl}phenyl)prop-2-enoate To a solution of triethylphosphono acetate (2.16 g; 9.66 mmol) in 100 mL of THF at 0° C. was added NaH (441 mg; 11.0 mmol). The reaction mixture was stirred for 30 min at 0° C., a solution of the previous aldehyde (3.40 g; 9.20 mmol) in 10 mL THF was then cannulated and the final mixture was stirred at rt for 12 h. The reaction was quenched using saturated aqueous NH$_4$Cl, the THF was removed in vacuo, extracted with CH$_2$Cl$_2$. The organic phase was washed with H$_2$O, saturated aqueous NaHCO$_3$, dried over Na$_2$SO$_4$, filtered and concentrated. Flash chromatography (Tol:EtOAc; 95:5) afforded the title compound as a yellow solid (3.54 g; 88%). $^1$H NMR (CDCl$_3$) δ 1.25 (3H, t), 4.20 (2H, q), 6.45 (1H, d), 7.1–7.5 (8H, m), 7.55 (3H, m), 7.67 (2H, m), 7.83 (1H, d), 7.89 (1H, d), 8.05 (1H, d).

Step 3: (E)-3-(2-{3-[2-(7-chloro-2-quinolyl)vinyl]phenyl}phenyl)prop-2-enoic acid To a solution of the previous ester (3.54 g; 8.05 mmol) in 50 mL of 1,4-dioxane was added 4 mL of NaOH (10 M). The mixture was stirred at 90° C. for 12 h, cooled down and acidified using HCl 10%. The residual precipitate (HCl salt of the quinoline) was filtered, washed with Et$_2$O and dried in vacuo to yield the title compound (3.5 g; 97%) which was used without further purification. $^1$H NMR (dmso-d$_6$) δ 6.49 (1H, d), 7.28 (1H, d), 7.4–8.0 (14H, m), 8.38 (1H, d).

Step 4: (E)-3-(2-{3-[2-(7-chloro(2-quinolyl))vinyl]phenyl}phenyl)-N-(2-thienyl sulfonyl)prop-2-enamide Prepared as described in Example 4, from the previous acid, 2-thiophenesulfonamide. $^1$H NMR (dmso-d$_6$) δ 6.63 (1H, d), 7.15 (1H, m), 7.25 (1H, d), 7.4–8.0 (16H, m), 8.40 (1H, d).

Example 8

(E)-3-[2-(3,4-Dichlorophenyl)phenyl]-N-(2-thienylsulfonyl)prop-2-enamide (104)

Step 1; Methyl (E)-3-[2-(3,4-dichlorophenyl)phenyl]prop-2-enoate

A mixture of 3,4-dichlorophenyl boronic acid (3.95 g; 25 mmol), ethyl 2-bromocinnamate (2.0 g; 8.3 mmol), CsF (6.30 g; 50 mmol) and Pd(PPh$_3$)$_4$ (1.21 g; 1.1 mmol) in 40 mL of DME was stirred at 100° C. for 10 h. The mixture was cooled to rt, poured in saturated aqueous NH$_4$Cl then extracted with EtOAc (2×). The combined organic extracts were dried over Na$_2$SO$_4$, filtered and concentrated. Flash chromatography (Tol) and subsequent swish (Hex) afforded the title compound (1.71 g; 47%). $^1$H NMR (CDCl$_3$) δ 3.75 (3H, s), 6.39 (1H, d), 7.12 (1H, dd), 7.30 (1H, m), 7.42 (3H, m), 7.50 (1H, d), 7.62 (1H, d), 7.68 (1H, m).

Step 2; (E)-3-[2-(3,4-dichlorophenyl)phenyl]prop-2-enoic acid

Prepared as described in Example 2 (step 2) from the previous ester. $^1$H NMR (CDCl$_3$) δ 6.40 (1H, d), 7.11 (1H, dd), 7.32 (1H, dd), 7.4–7.5 (4H, m), 7.70 (2H, m).

Step 3;(E)-3-[2-(3,4-dichlorophenyl)phenyl]-N-(2-thienylsulfonyl)prop-2-enamide

Prepared as described in Example 4 from the previous acid. $^1$H NMR (CDCl$_3$) δ 6.44 (1H, d), 7.04 (1H, dd), 7.10 (1H, dd), 7.3–7.5 (5H, m), 7.66 (3H, m), 7.90 (1H, dd). HRMS (FAB$^+$) m/z calcd for C$_{19}$H$_{14}$Cl$_2$NO$_3$S$_2$ (M+H$^+$): 437.9792, found 437.9791.

| | ELEMENTARY ANALYSIS OF REPRESENTATIVE COMPOUNDS | | | | | |
|---|---|---|---|---|---|---|
| | | Calculate (%) | | Observed (%) | | |
| | Molecular Formula | C | H | N | C | H | N |
| 1 | C$_{28}$H$_{21}$Cl$_2$NaO$_3$.H$_2$O | 65.00 | 4.48 | | 65.28 | 4.39 | |
| 2 | C$_{29}$H$_{25}$NaO$_3$.H$_2$O | 75.31 | 5.88 | | 75.61 | 5.71 | |

-continued

ELEMENTARY ANALYSIS OF REPRESENTATIVE COMPOUNDS

|  | Molecular Formula | Calculate (%) C | H | N | Observed (%) C | H | N |
|---|---|---|---|---|---|---|---|
| 3 | $C_{26}H_{21}NaO_3S.H_2O$ | 68.71 | 5.10 |  | 68.6 | 5.00 |  |
| 4 | $C_{26}H_{21}NaO_3S.0.5H_2O$ | 70.13 | 4.93 |  | 69.93 | 4.94 |  |
| 5 | $C_{27}H_{21}ClNNaO_3.4.5H_2O$ | 59.29 | 5.53 | 2.56 | 59.30 | 5.32 | 2.54 |
| 7 | $C_{28}H_{21}NaO_3.1.5H_2O$ | 73.84 | 5.31 |  | 73.60 | 5.11 |  |
| 8 | $C_{27}H_{21}NO_3$ | 79.59 | 5.19 | 3.44 | 79.37 | 5.30 | 3.41 |
| 9 | $C_{26}H_{19}Cl_2NaO_3S.H_2O$ | 59.66 | 4.04 |  | 59.49 | 4.26 |  |
| 11 | $C_{25}H_{19}NaO_2.0.5H_2O$ | 78.31 | 5.26 |  | 77.79 | 5.23 |  |
| 12 | $C_{21}H_{17}NaO_2$ | 77.76 | 5.28 |  | 77.40 | 5.96 |  |
| 13 | $C_{29}H_{25}NaO_3.H_2O$ | 75.31 | 5.88 |  | 75.85 | 5.68 |  |
| 14 | $C_{21}H_{15}Cl_2NaO_2.0.5H_2O$ | 62.70 | 4.01 |  | 62.22 | 3.93 |  |
| 15 | $C_{26}H_{21}NaO_3S.0.5H_2O$ | 70.10 | 4.98 |  | 70.21 | 5.30 |  |
| 16 | $C_{28}H_{23}NaO_3.0.5H_2O$ | 76.52 | 5.50 |  | 76.35 | 5.50 |  |
| 17 | $C_{28}H_{23}NaO_3.0.5H_2O$ | 76.52 | 5.50 |  | 76.08 | 5.51 |  |
| 18 | $C_{32}H_{25}NaO_3.H_2O$ | 77.09 | 5.46 |  | 77.41 | 5.41 |  |
| 19 | $C_{26}H_{19}NaO_3S.1.5H_2O$ | 67.67 | 4.80 |  | 68.00 | 4.69 |  |
| 20 | $C_{26}H_{19}NaO_3S.1.5H_2O$ | 67.67 | 4.80 |  | 67.82 | 4.91 |  |
| 21 | $C_{28}H_{23}NaO_3.0.5H_2O$ | 76.52 | 5.50 |  | 76.75 | 5.90 |  |
| 53 | $C_{32}H_{25}NO_4S_2$ | 69.67 | 4.57 | 2.54 | 69.20 | 4.63 | 2.54 |
| 72 | $C_{28}H_{26}NNaO_3S_3.0.5H_2O$ | 60.91 | 4.93 | 2.54 | 61.08 | 4.77 | 2.72 |
| 73 | $C_{28}H_{26}NNaO_3S_3.0.5H_2O$ | 60.91 | 4.93 | 2.54 | 61.05 | 4.68 | 2.51 |
| 75 | $C_{37}H_{36}NNaO_5S_3$ | 64.05 | 5.23 | 2.02 | 63.97 | 5.56 | 1.99 |
| 76 | $C_{37}H_{36}NNaO_6S_3.0.5H_2O$ | 61.82 | 5.19 | 1.95 | 61.74 | 5.26 | 1.86 |
| 77 | $C_{29}H_{28}NNaO_5S_2$ | 62.46 | 5.06 | 2.51 | 62.18 | 5.11 | 2.52 |
| 79 | $C_{32}H_{25}N_2NaO_3S_2.0.5H_2O$ | 66.08 | 4.51 | 4.82 | 65.83 | 4.75 | 4.72 |
| 80 | $C_{35}H_{32}NNaO_3S_3.H_2O$ | 64.49 | 5.22 | 2.15 | 64.55 | 5.28 | 2.10 |
| 81 | $C_{30}H_{30}NNaO_5S_2.0.5H_2O$ | 62.05 | 5.38 | 2.41 | 61.80 | 5.32 | 2.38 |
| 82 | $C_{38}H_{38}NNaO_6S_2$ | 65.97 | 5.54 | 2.02 | 65.95 | 5.20 | 2.14 |
| 83 | $C_{39}H_{32}ClN_2NaO_5S_2.H_2O$ | 62.52 | 4.57 | 3.74 | 62.66 | 4.49 | 3.65 |
| 84 | $C_{36}H_{33}ClNNaO_5S_2$ | 63.38 | 4.88 | 2.05 | 63.70 | 4.83 | 2.21 |
| 85 | $C_{41}H_{36}NNaO_6S_2.3H_2O$ | 63.14 | 5.43 | 1.80 | 63.14 | 4.95 | 1.96 |
| 86 | $C_{29}H_{28}NNaO_5S_2.H_2O$ | 60.51 | 5.25 | 2.43 | 60.88 | 5.00 | 2.53 |
| 87 | $C_{29}H_{26}NNaO_5S_2.0.5H_2O$ | 61.69 | 4.82 | 2.48 | 61.59 | 5.01 | 2.52 |
| 88 | $C_{29}H_{27}N_2NaO_4S_2.H_2O$ | 60.82 | 5.10 | 4.89 | 60.80 | 5.04 | 5.01 |
| 89 | $C_{29}H_{22}ClN_2NaO_4S_2.H_2O$ | 57.76 | 4.01 | 4.64 | 57.95 | 3.94 | 4.63 |
| 90 | $C_{20}H_{18}NNaO_3S_3.H_2O$ | 52.50 | 4.41 | 3.06 | 52.77 | 4.50 | 3.17 |
| 91 | $C_{20}H_{18}NNaO_5S_3.H_2O$ | 49.06 | 4.12 | 2.86 | 49.07 | 4.03 | 2.87 |
| 92 | $C_{29}H_{26}Br_2ClN_2NaO_5S_2.H_2O$ | 47.49 | 3.85 | 1.91 | 47.55 | 3.64 | 1.93 |
| 93 | $C_{39}H_{32}ClN_2NaO_5S_2.1.5H_2O$ | 61.70 | 4.46 | 3.70 | 61.77 | 4.65 | 3.69 |
| 94 | $C_{30}H_{22}ClN_2NaO_3S_2.H_2O$ | 60.15 | 4.03 | 4.68 | 59.95 | 4.05 | 4.56 |

Assays for Determining Biological Activity

The compounds of Formula I can be tested using the following assays to determine their prostanoid antagonist or agonist activity in vitro and in vivo and their selectivity. The prostaglandin receptors investigated were DP, $EP_1$, $EP_2$, $EP_3$, $EP_4$, FP, IP and TP.

Stable Expression of Prostanoid Receptors in the Human Embryonic Kidney (HEK) 293(Ebna) Cell Line Prostanoid receptor cDNAs corresponding to full length coding sequences were subcloned into the appropriate sites of mammalian expression vectors and transfected into HEK 293(ebna) cells. HEK 293(ebna) cells expressing the individual cDNAs were grown under selection and individual colonies were isolated after 2–3 weeks of growth using the cloning ring method and subsequently expanded into clonal cell lines.

Prostanoid Receptor Binding Assays

HEK 293(ebna) cells are maintained in culture, harvested and membranes are prepared by differential centrifugation, following lysis of the cells in the presence of protease inhibitors, for use in receptor binding assays. Prostanoid receptor binding assays are performed in 10 mM MES/KOH (pH 6.0) (EPs, FP and TP) or 10 mM HEPES/KOH (pH 7.4) (DP and IP), containing 1 mM EDTA, 10 mM divalent cation and the appropriate radioligand. The reaction is initiated by addition of membrane protein. Ligands are added in dimethylsulfoxide which is kept constant at 1% (v/v) in all incubations. Non-specific binding is determined in the presence of 1 $\mu$M of the corresponding non-radioactive prostanoid. Incubations are conducted for 60 min at room temperature or 30° C. and terminated by rapid filtration. Specific binding is calculated by subtracting non specific binding from total binding. The residual specific binding at each ligand concentration is calculated and expressed as a function of ligand concentration in order to construct sigmoidal concentration-response curves for determination of ligand affinity.

Prostanoid Receptor Agonist and Antagonist Assays

Whole cell second messenger assays measuring stimulation ($EP_2$, $EP_4$, DP and IP in HEK 293(ebna) cells) or inhibition ($EP_3$ in human erythroleukemia (HEL) cells) of intracellular cAMP accumulation or mobilization of intracellular calcium ($EP_1$, FP and TP in HEK 293(ebna) cells stably transfected with apo-aequorin) are performed to determine whether receptor ligands are agonists or antagonists. For cAMP assays, cells are harvested and resuspended in HBSS containing 25 mM HEPES, pH 7.4. Incubations contain 100 $\mu$M RO-20174 (phosphodiesterase type IV inhibitor, available from Biomol) and, in the case of the $EP_3$ inhibition assay only, 15 $\mu$M forskolin to stimulate cAMP production. Samples are incubated at 37° C. for 10 min, the reaction is terminated and cAMP levels are then measured. For calcium mobilization assays, cells are charged with the co-factors reduced glutathione and coelenterazine, harvested and resuspended in Ham's F12 medium. Calcium mobilization is measured by monitoring luminescence provoked by calcium binding to the intracellular photoprotein aequorin. Ligands are added in dimethylsulfoxide which is kept constant at 1% (v/v) in all incubations. For agonists, second messenger responses are expressed as a function of ligand concentration and both $EC_{50}$ values and the maximum response as compared to a prostanoid standard are calculated. For antagonists, the ability of a ligand to inhibit an agonist response is determined by Schild analysis and both $K_B$ and slope values are calculated.

Rat Paw Edema Assay

The method is the same as described in Chan et al (J. Pharmacol. Exp. Ther. 274: 1531–1537, 1995).

LPS-Induced Pyrexia in Conscious Rats

The method is the same as described in Chan et al (J. Pharmacol. Exp. Ther. 274: 1531–1537, 1995).

LPS-Induced Pyrexia in Conscious Squirrel Monkeys

The method is the same as described in Chan et al (Eur. J. Pharmacol. 327: 221–225, 1997).

Acute Inflammatory Hyperalgesia Induced by Carrageenan in Rats

The method is the same as described in Boyce et al (Neuropharmacology 33: 1609–1611, 1994).

Adjuvant-Induced Arthritis in Rats

Female Lewis rats (body weight~146–170 g) were weighed, ear marked, and assigned to groups (a negative control group in which arthritis was not induced, a vehicle control group, a positive control group administered indomethacin at a total daily dose of 1 mg/kg and four groups administered with a test compound at total daily doses of 0.10–3.0 mg/kg) such that the body weights were equivalent within each group. Six groups of 10 rats each were injected into a hind paw with 0.5 mg of *Mycobacterium butyricum* in 0.1 mL of light mineral oil (adjuvant), and a negative control group of 10 rats was not injected with adjuvant. Body weights, contralateral paw volumes (determined by mercury displacement plethysmography) and lateral radiographs (obtained under Ketamine and Xylazine anesthesia) were determined before (day −1) and 21 days following adjuvant injection, and primary paw volumes were determined before (day −1) and on days 4 and 21 following adjuvant injection. The rats were anesthetized with an intramuscular injection of 0.03–0.1 mL of a combination of Ketamine (87 mg/kg) and Xylazine (13 mg/kg) for radiographs and injection of adjuvant. The radiographs were made of both hind paws on day 0 and day 21 using the Faxitron (45 kVp, 30 seconds) and Kodak X-OMAT TL film, and were developed in an automatic processor. Radiographs were evaluated for changes in the soft and hard tissues by an investigator who was blinded to experimental treatment. The following radiographic changes were graded numerically according to severity: increased soft issue volume (0–4), narrowing or widening of joint spaces (0–5) subchondral erosion (0–3), periosteal reaction (0–4), osteolysis (0–4) subluxation (0–3), and degenerative joint changes (0–3). Specific criteria were used to establish the numerical grade of severity for each radiographic change. The maximum possible score per foot was 26. A test compound at total daily doses of 0.1, 0.3, 1, and 3 mg/kg/day, indomethacin at a total daily dose of 1 mg/kg/day, or vehicle (0.5% methocel in sterile water) were administered per os b.i.d. beginning post injection of adjuvant and continuing for 21 days. The compounds were prepared weekly, refrigerated in the dark until used, and vortex mixed immediately prior to administration.

What is claimed is:

1. A method of treating a prostaglandin E mediated disease which comprises administering to a mammalian patient in need of such treatment or prevention a compound of formula I:

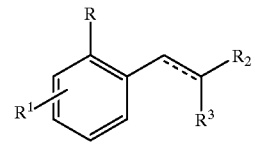

wherein:

R is a group Ar as defined hereinafter;

$R^1$ is hydrogen, hydroxy, $C_{1-6}$alkyl, $C_{1-6}$alkoxy, $X(CH_2)_p$Ar, or a methylenedioxy group attached to two adjacent ring carbon atoms;

$R^2$ is —$(CH_2)_xC(O)N(R^4)S(O)_yR^5$, —$(CH_2)_xS(O)_yN(R^4)C(O)R^5$, —$(CH_2)_xC(O)N(R^4)C(O)R^5$, —$(CH_2)_xS(O)_yN(R^4)S(O)_yR^5$, —$(CH_2)_xCO_2R^4$, or tetrazol-5-yl optionally substituted by $C_{1-6}$alkyl;

$R^3$ is $X(CH_2)_pAr$ or $X(CH_2)_pR^4$ or a group of formula (a):

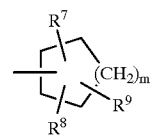

Ar is a group of formula (b) or (c):

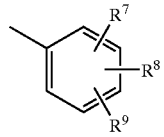

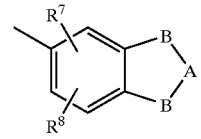

or Ar is naphthyl, which may be unsubstituted or substituted by one or more $R^7$ or $R^8$ groups;

A is C=O or $(C(R^4)_2)m$;

each B is —$CH_2$—;

$R^4$ is hydrogen or $C_{1-6}$alkyl, with the proviso that when $R^7$ or $R^9$ is X—$(CR^4)_p$—$OR^4$, X is $(CH_2)_p$ and p is 0 then $R^4$ is not $C_{1-6}$alkyl;

$R^5$ is hydrogen or $C_{1-10}$alkyl or Ar, both of which may be unsubstituted or substituted by one or two Cl, F, Br, hydroxy, $XC_{1-5}$alkyl, $C_{1-5}$alkyl, $NO_2$, tetrazol-5-yl optionally substituted by $C_{1-6}$alkyl, or $R^5$ is $N(R^4)_2$;

$R^6$ is $R^{10}$, $CO_2R^{11}$, $CO_2C(R^{10})_2O(CO)XR^{11}$, $PO_3(R^{11})_2$, $SO_2NR^{11}R^{10}$, $NR^{11}SO_2R^{10}$, $CONR^{11}SO_2R^{10}$, $SO_3R^{11}$, $S(O)_qR^{11}$, $S(O)_qN(R^{11})C(O)R^{10}$, $S(O)_qN(R^{11})S(O)_qR^{10}$, $C(O)N(R^{11})C(O)R^{10}$, $N(R^{11})C(O)R^{10}$, $N(R^{11})_2$, $N(R^{11})C(O)NR^{11}$, $P(O)(OR^{11})R^{11}$, CN, —$CO_2(CH_2)_mC(O)N(R^4)_2$, $C(R^{10})_2N(R^{11})_2$, $C(O)N(R^4)_2$, $OR^4$ or tetrazolyl optionally substituted by C1–6 alkyl, with the proviso that when $R^7$ or $R^9$ is —X—$(CH_2)_p$—$R^6$, p is 0 and X is $(CH_2)_p$ then $R^6$ is not $S(O)_qR^{11}$;

$R^7$ and $R^9$ are independently $R^{10}$, OH, $C_{1-8}$ alkoxy, $S(O)_qR^{10}$, Br, F, I, Cl, $CF_3$, $NO_2$, $NHCOR^4$, $R^{12}CO_2R^{11}$, —X—$R^{13}$—Y, —$X(CR^4)_pR^4$, $S(CH_2)_p$ $CO_2H$, $(CH_2)_pX$—$R^{13}$—, $X(CH_2)_pCONR^{11}$ $SO_2R^{10}$, $(CH_2)_pXCONR^{11}SO_2R^{10}$ or $X(CH_2)_pR^6$ wherein each methylene group within —$X(CH_2)_qR^6$ may be unsubstituted or substituted by one or two —$(CH_2)_pAr$ groups;

$R^8$ is hydrogen, $R^{10}$, OH, $C_{1-5}$alkoxy, $S(O)_qR^{10}$, $N(R^4)_2$, Br, F, I, Cl or $NHCOR^4$ wherein the $C_{1-5}$ alkoxy may be unsubstituted or substituted by OH, methoxy or halogen;

$R^{10}$ is hydrogen, Ar, $C_{1-10}$alkyl, $C_{2-10}$alkenyl, $C_{2-10}$alkynyl, all of which may be unsubstituted or substituted by one or more $OH, CH_2OH, N(R^4)_2$ or halogen; or $R^{10}$ is $N(R^4)_2$;

$R^{11}$ is independently hydrogen, $C_{1-10}$alkyl, $C_{2-10}$alkenyl or $C_{2-8}$alkynyl, all of which may be unsubstituted or substituted by one or more OH, $N(R^4)_2$, $CO_2R^{14}$, halogen or $XC_{1-5}$alkyl; or $R^{11}$ is $(CH_2)_pAr$;

$R^{12}$ is divalent Ar, $C_{1-10}$alkylene, $C_{1-10}$alkylidene, $C_{2-10}$alkenylene, $C_{2-10}$alkynylene, all of which may be unsubstituted or substituted by one or more of OH, $CH_2OH$, $N(R^4)_2$ or halogen;

$R^{13}$ is selected from the group consisting of:
(1) a bond,
(2) when $R^{13}$ is a linking group, selected from the group consisting of $C_{1-10}$alkylene, $C_{1-10}$alkenylene, $C_{1-10}$alkylidene, $C_{1-10}$alkynylene, all of which may be linear or branched, or phenylene, all of which may be unsubstituted or substituted by one or more OH, $N(R^4)_2$, COOH or halogen, and
(3) when $R^{13}$ is a terminal group, selected from the group consisting of $C_{1-10}$alkyl, $C_{1-10}$alkenyl, $C_{1-10}$alkynyl, all of which may be linear or branched, or phenyl, all of which may be unsubstituted or substituted by one or more OH, $N(R^4)_2$, COOH or halogen, with the proviso that when $R^7$ or $R^9$ is —$(CH_2)_p$—X—$R^{13}$, p is 0 and X is O then $R^{13}$ is not a linear or branched alkyl chain of 1 to 8 carbon atoms;

$R^{14}$ is hydrogen, $C_{1-6}$alkyl, $C_{2-6}$alkenyl or $C_{2-7}$alkynyl;

X is $(CH_2)_p$, O, $NR^4$ or $S(O)_p$;

Y is $CH_3$ or $X(CH_2)_pAr$, with the proviso that when $R^7$ or $R^9$ is X—$R^{13}$—Y, X is O and $R^{13}$ is a bond, then Y is not $CH_3$;

q is zero, one or two;

p is an integer from 0 to 6;

m is 1, 2 or 3;

n is 1 to 4;

x is 0 to 4;

y is 1 or 2;

the dotted line signifies the optional presence of a bond such that it represents a single or double bond.

2. A method of treating a prostaglandin E mediated disease which comprises administering to a mammalian patient in need of such treatment or prevention a compound of formula I:

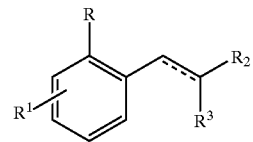

wherein:

R is a group Ar as defined hereinafter;

$R^1$ is hydrogen, hydroxy, $C_{1-6}$alkyl, $C_{1-6}$alkoxy, $X(CH_2)_pAr$, or a methylenedioxy group attached to two adjacent ring carbon atoms;

$R^2$ is —$(CH_2)_xC(O)N(R^4)S(O)_yR^5$, —$(CH_2)_xS(O))_yN(R^4)C(O)R^5$, —$(CH_2)_xC(O)N(R^4)C(O)R^5$, —$(CH_2)_xS(O)_yN(R^4)S(O)_yR^5$, —$(CH_2)_xCO_2R^4$, or tetrazol-5-yl optionally substituted by $C_{1-6}$alkyl;

$R^3$ is $X(CH_2)_pAr$ or $X(CH_2)_pR^4$ or a group of formula (a):

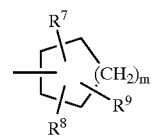

(a)

Ar is a group of formula (b) or (C):

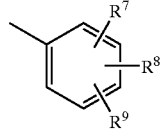

(b)

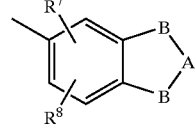

(c)

or Ar is naphthyl, which may be unsubstituted or substituted by one or more $R^7$ or $R^8$ groups;

A is C=O or $(C(R^4)_2)m$;

each B is —$CH_2$—;

$R^4$ is hydrogen or $C_{1-6}$alkyl, with the proviso that when $R^7$ or $R^9$ is X—$(CR^4)_p$—$OR^4$, X is $(CH_2)_p$ and p is 0 then $R^4$ is not $C_{1-6}$alkyl;

$R^5$ is hydrogen or $C_{1-6}$alkyl or Ar, both of which may be unsubstituted or substituted by one or two Cl, F, Br, hydroxy, $XC_{1-5}$alkyl, $C_{1-5}$alkyl, $NO_2$, tetrazol-5-yl optionally substituted by $C_{1-6}$alkyl, or $R^5$ is $N(R^4)_2$;

$R^6$ is $R^{10}$, $CO_2R^{11}$, $CO_2C(R^{10})_2O(CO)XR^{11}$, $PO_3(R^{11})_2$, $SO_2NR^{11}R^{10}$, $NR^{11}SO_2R^{10}$, $CONR^{11}$ $SO_2R^{10}$, $SO_3R^{11}$, $S(O)_qR^{11}$, $S(O)_qN(R^{11})C(O)R^{10}$, $S(O)_qN(R^{11})$ $S(O)_qR^{10}$, $C(O)N(R^{11})C(O)R^{10}$, $N(R^{11})C(O)R^{10}$, $N(R^{11})_2$, $N(R^{11})C(O)NR^{11}$, $P(O)(OR^{11})R^{11}$, CN, —$CO_2(CH_2)_mC(O)N(R^4)_2$, $C(R^{10}O)_2N(R^{11})_2$, $C(O)N(R^4)_2$, $OR^4$ or tetrazolyl optionally substituted by C1–6 alkyl, with the proviso that when $R^7$ or $R^9$ is —X—$(CH_2)_p$—$R^6$, p is 0 and X is $(CH_2)_p$ then $R^6$ is not $S(O)_qR^{11}$;

$R^7$ and $R^9$ are independently $R^{10}$, OH, $C_{1-8}$alkoxy, $S(O)_q$ $R^{10}$, Br, F, I, Cl, $CF_3$, $NO_2$, $NHCOR^4$, $R^{12}CO_2R^{11}$, —X—$R^{13}$—Y, —X(CR$^4$)$_p$OR$^4$, S(CH$_2$)$_p$CO$_2$H, (CH$_2$)$_p$ X—$R^{13}$, —X(CH$_2$)$_p$CONR$^{11}$SO$_2$R$^{10}$, (CH$_2$)$_p$ XCONR$^{11}$SO$_2$R$^{10}$ or X(CH$_2$)$_p$R$^6$ wherein each methylene group within —X(CH$_2$)$_q$R$^6$ may be unsubstituted or substituted by one or two —(CH$_2$)$_p$Ar groups;

$R^8$ is hydrogen, $R^{10}$, OH, C$_{1-5}$alkoxy, S(O)$_q$R$^{10}$, N(R$^4$)$_2$, Br, F, I, Cl or NHCOR$^4$ wherein the C$_{1-5}$alkoxy may be unsubstituted or substituted by OH, methoxy or halogen;

$R^{10}$ is hydrogen, Ar, C$_{1-10}$alkyl, C$_{2-10}$alkenyl, C$_{2-10}$alkynyl, all of which may be unsubstituted or substituted by one or more OH, CH$_2$OH, N(R$^4$)$_2$ or halogen; or $R^{10}$ is N(R$^4$)$_2$;

$R^{11}$ is independently hydrogen, C$_{1-10}$alkyl, C$_{2-10}$alkenyl or C$_{2-8}$alkynyl, all of which may be unsubstituted or substituted by one or more OH, N(R$^4$)$_2$, CO$_2$R$^{14}$, halogen or XC$_{1-5}$alkyl; or $R^{11}$ is (CH$_2$)$_p$Ar;

$R^{12}$ is divalent Ar, C$_{1-10}$alkylene, C$_{1-10}$alkylidene, C$_{2-10}$alkenylene, C$_{2-10}$alkynylene, all of which may be unsubstituted or substituted by one or more of OH, CH$_2$OH, N(R$^4$)$_2$ or halogen;

$R^{13}$ is selected from the group consisting of:
(1) a bond,
(2) $R^{13}$ is a linking group, selected from the group consisting of C$_{1-10}$alkylene, C$_{1-10}$alkylene, C$_{1-10}$alkylidene, C$_{1-10}$alkynylene, all of which may be linear or branched, or phenylene, all of which may be unsubstituted of substituted by one or more OH, N(R$^4$)$_2$, COOH or halogen, and
(3) when $R^{13}$ is a terminal group, selected from the group consisting of C$_{1-10}$alkyl, C$_{1-10}$alkylenyl, C$_{1-10}$alkynyl, all of which may be linear or branched, or phenyl, all of which may be unsubstituted or substituted by one or more OH, N(R$^4$)$_2$, COOH or halogen, with the proviso that when R$^7$ or R$^9$ is —(CH$_2$)$_2$—X—$R^{13}$, p is 0 and X is O then $R^{13}$ is not a linear or branched alkyl chain of 1 to 8 carbon atoms;

$R^{14}$ is hydrogen, C$_{1-6}$alkyl, C$_{2-6}$alkenyl, C$_{2-7}$alkynyl;
X is (CH$_2$)$_p$, O, NR$^4$ or S(O)$_p$;

Y is (CH$_3$) or X(CH$_2$)$_p$Ar, with the proviso that when R$^7$ or R$^9$ is X—$R^{13}$—Y, X is O and $R^{13}$ is a bond, then Y is not CH$_3$;

q is zero, one or two;
p is an integer from 0 to 6;
m is 1, 2 or 3;
n is 1 to 4;
x is 0 to 4;
y is 1 to 2;
the dotted line signifies the optional presence of a bond such that it represents a single or double bond,
wherein the prostaglandin mediated disease is selected from the group consisting of:
(1) pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures as well as immune and autoimmune diseases; and
(2) thrombosis.

3. A method according to claim 2 wherein the prostaglandin mediated disease is selected from the group consisting of: pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures as well as immune and autoimmune diseases.

4. A method according to claim 3 wherein the prostaglandin mediated disease is pain, fever or inflammation associated with dysmenorrhea.

5. A compound selected from one of the following tables:

TABLE 1

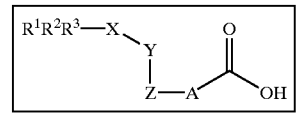

| R$^1$ | R$^2$ | R$^3$ | X | Y(R$^{7,8}$) | Z(R$^{7,8}$) | A | Cpd |
|---|---|---|---|---|---|---|---|
| 2-(2,6-Cl$_2$-benzyloxy) | H | H | benzene diyl | 1,3 benzene diyl | 1,2 benzene diyl | CH$_2$—CH$_2$ | 1 |
| 2-Benzyl oxy | H | H | benzene diyl | 1,3 benzene diyl | 1,2 benzene diyl | CH$_2$—CH(CH$_3$) | 2 |
| 2-Benzyl oxy | H | H | benzene diyl | 1,3 benzene diyl | 1,2 benzene diyl | CH=CH | 7 |
| H | H | H | naphthyl | 1,3 benzene diyl | 1,2 benzene diyl | CH$_2$—CH$_2$ | 11 |
| H | H | H | phenyl | 1,3 benzene diyl | 1,2 benzene diyl | CH$_2$—CH$_2$ | 12 |
| 2-Benzyl oxy | H | H | benzene diyl | 1,3 benzene diyl | 1,2 benzene diyl | CH$_2$—CH$_2$—CH$_2$ | 13 |
| 2-Chloro | 3-Cl | H | benzene triyl | 1,3 benzene diyl | 1,2 benzene diyl | CH$_2$—CH$_2$ | 14 |
| 2-Phenoxy methyl | H | H | benzene diyl | 1,3 benzene diyl | 1,2 benzene diyl | CH$_2$—CH$_2$ | 16 |
| 4-Benzyl | H | H | benzene diyl | 1,3 benzene diyl | 1,2 benzene diyl | CH$_2$—CH$_2$ | 17 |

TABLE 1-continued $R^1R^2R^3-X-Y-Z-A-C(O)OH$

| R¹ | R² | R³ | X | Y(R⁷,⁸) | Z(R⁷,⁸) | A | Cpd |
|---|---|---|---|---|---|---|---|
| oxy | | | diyl | diyl | diyl | | |
| 4-Benzyloxy | H | H | 1-naphthalenediyl | 1,3 benzenediyl | 1,2 benzenediyl | $CH_2-CH_2$ | 18 |
| 2-Benzyloxy | H | H | benzenediyl | 1,3 benzenediyl | 1,2 benzenediyl | $CH_2-CH_2$ | 21 |
| 2-Benzyloxy | H | H | benzenediyl | 2,6-pyridinediyl | 1,2 benzenediyl | $CH=CH$ | 38 |
| 2-Benzyloxy | H | H | benzenediyl | 1,3-benzenetriyl (5-Cl) | 1,2 benzenetriyl (4-F) | $CH=CH$ | 41 |
| 2-Benzyloxy | H | H | benzenediyl | 1,3-benzenetriyl (5-OCF₃) | 1,2 benzenetriyl (4-Cl) | $CH=C(CH_3)$ | 42 |
| 2-Benzyloxy | H | H | benzenediyl | 1,3-benzenetriyl (5-CN) | 1,2 benzenetriyl (5-Cl) | $CH_2-CH_2$ | 43 |
| 2-Benzyloxy | H | H | benzenediyl | 1,3-benzenetriyl (5-Me) | 1,2 benzenetriyl (5-OMe) | $CH=CH$ | 44 |
| 2-Benzyloxy | H | H | benzenediyl | 1,3-benzenetriyl (2-Me) | 1,2 benzenetriyl (6-Cl) | $CH=C(CH_3)$ | 45 |
| 2-Benzyloxy | H | H | benzenediyl | 1,3-benzenetriyl (2-OMe) | 1,2 benzenetriyl (6-OMe) | $CH_2-CH_2$ | 46 |

TABLE 2

$R^1R^2R^3-X-Y-Z-A-C(O)-NH-S(O)_2-R^5$

R², R³ = H,
Z = 1,2-benzenediyl

| R¹ | X | Y | A | R⁵ | Cpd |
|---|---|---|---|---|---|
| 2-Benzyloxy | benzenediyl | 1,3 benzenediyl | $CH=CH$ | 2-thienyl | 53 |
| 2-Benzyloxy | benzenediyl | 1,3-benzenediyl | $CH_2-C(CH_3)_2$ | styryl | 54 |
| 2-(4-MeO-benzyloxy) | benzenediyl | 3,5-thiophenediyl | $CH_2-CH(CH_3)$ | benzyl | 55 |
| 2-(2,3-Cl₂-benzyloxy) | benzenediyl | 1,3-benzenediyl | $CH=CH$ | cyclohexyl | 56 |
| 2-(4-CF₃-benzyloxy) | benzenediyl | 1,3-benzenediyl | $CH_2-CH(CH_3)$ | 4-Cl-phenyl | 58 |
| 2-(4-MeO-benzyloxy) | benzenediyl | 1,3-benzenediyl | $CH_2-C(CH_3)_2$ | 4-($CH_3SO_2$)phenyl | 60 |
| 2-Benzyloxy | benzenediyl | 1,3-benzenediyl | $CH=CH$ | 2-MeO-5-Br-phenyl | 62 |
| 2-(2,3-Cl₂-benzyloxy) | benzenediyl | 1,3-benzenediyl | $CH_2-CH(CH_3)$ | 3,4-Cl₂-phenyl | 64 |
| 2-(4-CF₃-benzyloxy) | benzenediyl | 1,3-benzenediyl | $CH_2-C(CH_3)_2$ | 3-Cl-4-F-phenyl | 66 |
| 2-(4-MeO-benzyloxy) | benzenediyl | 1,3-benzenediyl | $CH=CH$ | 1-imidazoyl | 68 |
| 2-Benzyloxy | benzenediyl | 1,3-benzenediyl | $CH_2-CH(CH_3)$ | 3-indolyl | 70 |

TABLE 3

$R^1R^2R^3-X-Y-A-C(O)-NH-S(O)_2-B$

R3 = H,

| R¹ | R² | X | Y(R⁷,⁸) | A | B | Cpd |
|---|---|---|---|---|---|---|
| 3-(2-Ph—Et—SCH₂) | H | benzenediyl | 1,2 benzenediyl | $CH_2-CH_2$ | 2-thienyl | 72 |

TABLE 3-continued

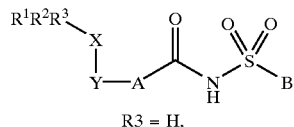

R3 = H,

| R¹ | R² | X | Y(R^{7,8}) | A | B | Cpd |
|---|---|---|---|---|---|---|
| 4-(2-Ph—Et—SCH$_2$) | H | benzene diyl | 1,2 benzene diyl | CH$_2$—CH$_2$ | 2-thienyl | 73 |
| 4-(2-Ph—Et—SCH$_2$) | H | benzene diyl | 1,2 benzene diyl | CH$_2$—CH$_2$—CH$_2$ | 2-thienyl | 74 |
| 4-(3(-3-(2-Ph—Et—SCH$_2$)Ph-oxy)Pr-oxy) | H | benzene diyl | 1,2 benzene diyl | CH$_2$—CH$_2$ | 2-thienyl | 75 |
| 4-(3(-3-(2-Ph—Et—S(O)—CH$_2$)Ph-oxy)Pr-oxy) | H | benzene diyl | 1,2 benzene diyl | CH$_2$—CH$_2$ | 2-thienyl | 76 |
| 4-(3-(3-Me—Ph-oxy)Pr-oxy) | H | benzene diyl | 1,2 benzene diyl | CH$_2$—CH$_2$ | 2-thienyl | 77 |
| 4-(3(-3-(2-Ph—Et-S(O)$_2$—CH$_2$)Ph-oxy)Pr-oxy) | H | benzene diyl | 1,2 benzene diyl | CH$_2$—CH$_2$ | 2-thienyl | 78 |
| 4-Carbazole-yl-CH$_2$ | H | benzene diyl | 1,2 benzene diyl | CH$_2$—CH$_2$ | 2-thienyl | 79 |
| 4-(2-Ph—Et—SCH$_2$) | H | benzene diyl | 1,2 benzene triyl (5-Bn) | CH$_2$—CH$_2$ | 2-thienyl | 80 |
| 4-(3-(3-Me—Ph-oxy)Pr-oxy) | H | benzene diyl | 1,2 benzene diyl | CH$_2$—CH(CH$_3$) | 2-thienyl | 81 |
| 4-(3-(3-(3-Ph)Pr-oxy CH$_2$)Ph-oxy)Pr-oxy) | H | benzene diyl | 1,2 benzene diyl | CH$_2$—CH$_2$ | 2-thienyl | 82 |
| 4-(3-(2-(Qn)ethenyl)Ph-oxy)Pr-oxy) | H | benzene diyl | 1,2 benzene diyl | CH$_2$—CH$_2$ | 2-thienyl | 83 |
| 4-(3-(3-2-((4-Cl—Ph)—Et)Ph-oxy)Pr-oxy) | H | benzene diyl | 1,2 benzene diyl | CH$_2$—CH$_2$ | 2-thienyl | 84 |
| 4-(3-(3-(4-Ph—Ph-oxy-CH$_2$)Ph-oxy)Pr-oxy) | H | benzene diyl | 1,2 benzene diyl | CH$_2$—CH$_2$ | 2-thienyl | 85 |
| 3-(3-(3-Me—Ph-oxy)Pr-oxy) | H | benzene diyl | 1,2 benzene diyl | CH$_2$—CH$_2$ | 2-thienyl | 86 |
| 4-(2-(3-Tolyl) acetoxy CH$_2$) | H | benzene diyl | 1,2 benzene diyl | CH$_2$—CH$_2$ | 2-thienyl | 87 |
| 4-(2-(3-Tolyl) acetamide CH$_2$) | H | benzene diyl | 1,2 benzene diyl | CH$_2$—CH$_2$ | 2-thienyl | 88 |
| 3-(3-(2-(Qn)CH$_2$ oxy) | H | benzene diyl | 1,2 benzene diyl | CH$_2$—CH$_2$ | 2-thienyl | 89 |
| 3-Thiomethyl | H | benzene diyl | 1,2 benzene diyl | CH$_2$—CH$_2$ | 2-thienyl | 90 |
| 3-Methylsulfone | H | benzene diyl | 1,2 benzene diyl | CH$_2$—CH$_2$ | 2-thienyl | 91 |
| 4-(3-(3-Me—Ph-oxy)Pr-oxy) | 3,5-Br | benzene tetrayl | 1,2 benzene diyl | CH$_2$—CH$_2$ | 2-thienyl | 92 |
| 3-(3-(2-(Qn)ethenyl)Ph-oxy)Pr-oxy) | H | benzene diyl | 1,2 benzene diyl | CH$_2$—CH$_2$ | 2-thienyl | 93 |
| 3-(2-(Qn)ethenyl) | H | benzene diyl | 1,2 benzene diyl | CH$_2$—CH$_2$ | 2-thienyl | 94 |
| 3-(3-(3-Me—Ph-oxy)Pr-oxy) | H | benzene diyl | 1,2 benzene diyl | CH$_2$—CH((CH$_2$)$_3$Ph) | 2-thienyl | 95 |
| 3-(2-Ph-2-oxy-ethoxy) | H | benzene diyl | 1,2 benzene diyl | CH$_2$—CH$_2$ | 2-thienyl | 96 |
| 3-(2-(3-Phenyl-Pr-oxy)2-Ph-ethoxy) | H | benzene diyl | 1,2 benzene diyl | CH$_2$—CH$_2$ | 2-thienyl | 97 |
| 3-(2-(Qn)ethenyl) | H | benzene diyl | 1,2 benzene diyl | CH═CH | 2-thienyl | 98 |
| 4-Chloro | 3-Cl | benzene triyl | 1,2 benzene diyl | CH═CH | 2-thienyl | 99 |
| 3-(2-(Qn)ethenyl) | H | benzene diyl | 1,2 benzene triyl (5-CF$_3$) | CH═CH | 2-thienyl | 100 |
| 3-(3-(3-Me—Ph-oxy)Pr-oxy) | H | benzene diyl | 1,2 benzene triyl (5-OMe) | CH═CH | 2-MeO-5-Br-phenyl | 101 |
| 4-Chloro | 3-Cl | benzene triyl | 1,2 benzene triyl (5-Me) | CH═CH | 3-Cl-4-F-phenyl | 102 |
| 3-(2-Ph—Et—SCH$_2$) | H | benzene diyl | 1,2 benzene triyl (5-Bn) | CH═CH | 2-thienyl | 103 |
| 3-(2-(Qn)ethenyl) | H | benzene | 1,2 benzene | CH═CH | 2-MeO-5-Br— | 104 |

TABLE 3-continued $$R^1R^2R^3X-Y-A-C(O)-N(H)-S(O)(O)-B$$

R3 = H,

| R¹ | R² | X | Y(R$^{7,8}$) | A | B | Cpd |
|---|---|---|---|---|---|---|
| | | diyl | triyl (6-Cl) | | Ph | |
| 3-(3-(3-Me—Ph-oxy)Pr-oxy) | H | benzene diyl | 1,2 benzene triyl (6-OMe) | CH=CH | 3-Cl-4-F-phenyl | 105 |
| 4-Chloro | 3-Cl | benzene triyl | 1,2 benzene triyl (3-Cl) | CH=CH | 2-thienyl | 106 |
| 3-(2-Ph—Et—SCH$_2$) | H | benzene diyl | 1,2 benzene triyl (3-OMe) | CH=CH | 2-MeO-5-Br—Ph | 107 |
| 3-(2-(Qn)ethenyl) | H | benzene diyl | 1,2 benzene triyl (4-F) | CH=CH | 3-Cl-4-F-phenyl | 108 |
| 3-(3-(3-Me—Ph-oxy)Pr-oxy) | H | benzene diyl | 1,2 benzene triyl (4-Cl) | CH=CH | 2-thienyl | 109 |
| 4-Chloro | 3-Cl | benzene triyl | 1,2 benzene diyl | CH=CH | 4-MeO-phenyl | 110 |
| 3-Ph—Et—SCH$_2$ | H | benzene diyl | 1,2 benzene diyl | CH=CH | 4-CF$_3$-phenyl | 111 |
| 3-(2-(Qn)ethenyl) | H | benzene diyl | 1,2 benzene diyl | CH=CH | 4-(CH$_3$SO$_2$) phenyl | 112 |
| 3-(3-(3-Me—Ph-oxy)Pr-oxy) | H | benzene diyl | 1,2 benzene diyl | CH=CH | 2-methyl phenyl | 113 |
| 4-Chloro | 3-Cl | benzene triyl | 1,2 benzene diyl | CH=CH | 2,3-Cl$_2$-phenyl | 114 |
| 3-(2-Ph—Et—SCH$_2$) | H | benzene diyl | 1,2 benzene diyl | CH=CH | 2-NO$_2$-4-Cl-phenyl | 115 |
| 3-(2-(Qn)ethenyl) | H | benzene diyl | 1,2 benzene diyl | CH=CH | 2,5-(CH$_3$)$_2$-phenyl | 116 |
| 3-(3-(3-Me—Ph-oxy)Pr-oxy) | H | benzene diyl | 1,2 benzene diyl | CH=CH | 2,6-F$_2$-phenyl | 117 |
| 4-Chloro | H | benzene diyl | 1,2 benzene diyl | CH=CH | 3,4-Cl$_2$-phenyl | 118 |
| 3-(2-Ph—Et—SCH$_2$) | H | benzene diyl | 1,2 benzene diyl | CH=CH | 3,5-Br$_2$-phenyl | 119 |
| 3-(2-(Qn)ethenyl) | H | benzene diyl | 1,2 benzene diyl | CH=CH | 2-thiazoyl | 120 | or pharmaceutically acceptable salt thereof,
 wherein
 Qn represents 7-chloro-quinol-2-yl,
 2-Ph-Et-SCH$_2$ represents 2-phenylethylthiomethyl, and
 3-(3-Me-Ph-oxy)Pr-oxy represents 3-(3-methylphenoxy)propyl-1-oxy.

* * * * *